US010646472B2

(12) United States Patent
Taratula et al.

(10) Patent No.: US 10,646,472 B2
(45) Date of Patent: May 12, 2020

(54) COMPOSITION COMPRISING A PHOTOSENSITIVE COMPOUND IN A POLYMERIC NANOPARTICLE, AND A METHOD OF USING THE COMPOSITION

(71) Applicant: Oregon State University, Corvallis, OR (US)

(72) Inventors: Olena Taratula, Portland, OR (US); Oleh Taratula, Portland, OR (US); Adam Alani, Salem, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 15/785,782

(22) Filed: Oct. 17, 2017

(65) Prior Publication Data

US 2018/0028496 A1 Feb. 1, 2018

Related U.S. Application Data

(63) Continuation-in-part of application No. PCT/US2016/028113, filed on Apr. 18, 2016.

(60) Provisional application No. 62/150,125, filed on Apr. 20, 2015.

(51) Int. Cl.
*A61K 9/00* (2006.01)
*A61K 31/409* (2006.01)
(Continued)

(52) U.S. Cl.
CPC ........ *A61K 31/409* (2013.01); *A61K 41/0071* (2013.01); *A61K 49/0036* (2013.01); *A61K 49/0093* (2013.01); *G01N 15/14* (2013.01)

(58) Field of Classification Search
CPC .................................................... A61K 31/409
See application file for complete search history.

(56) References Cited

U.S. PATENT DOCUMENTS

2010/0016227 A1 1/2010 Enright et al.
2011/0262356 A1* 10/2011 Bonacchi ........... A61K 49/0032 424/9.1
2013/0336889 A1 12/2013 Shieh et al.

FOREIGN PATENT DOCUMENTS

JP 2013199476 10/2013
WO WO 2009/107859 9/2009
(Continued)

OTHER PUBLICATIONS

Huang, "Polymeric complex micelle loaded with axially substituted silicon(IV) phthalocyanine," *Chinese Chemical Letters* 20(5):627-630, 2009.

(Continued)

*Primary Examiner* — Paul W Dickinson
(74) *Attorney, Agent, or Firm* — Klarquist Sparkman, LLP

(57) ABSTRACT

Embodiments of a composition comprising a photosensitive compound and a polymer nanoparticle are disclosed herein. The composition may further comprise a targeting moiety. In some embodiments, the photosensitive compound is a phthalocyanine or phthalocyanine derivative, such as a naphthalocyanine. Upon irradiation with near infrared light, the composition may be used as a fluorescent imaging agent and/or as a phototherapeutic agent, such as for photodynamic and/or photothermal therapies. In certain embodiments, the composition is used to treat certain cancers.

18 Claims, 21 Drawing Sheets
(7 of 21 Drawing Sheet(s) Filed in Color)
Specification includes a Sequence Listing.

(51) Int. Cl.

| | |
|---|---|
| ***A61K 41/00*** | (2020.01) |
| ***A61K 49/00*** | (2006.01) |
| *G01N 15/14* | (2006.01) |

(56) References Cited

FOREIGN PATENT DOCUMENTS

| | | |
|---|---|---|
| WO | WO 2013/012628 | 1/2013 |
| WO | WO 2015/026963 | 2/2015 |
| WO | WO 2017/031367 | 2/2017 |

OTHER PUBLICATIONS

Master et al., "Delivery of the Photosensitizer Pc4 in PEG-PCL Micelles for In Vitro PDT Studies," *Journal of Pharmaceutical Sciences* 99(5):2386-2398, 2010, published online Dec. 4, 2009.

Pan et al., "Photophysical property of a polymeric nanoparticle loaded with an aryl benzyl ester silicon (IV) phthalocyanine," *Twelfth International Conference on Photonics and Imaging in Biology and Medicine* (*PIBM 2014*), International Society for Optical Engineering, vol. 9230, p. 92300T, Sep. 17, 2014.

Sekkat et al., "Like a Bolt from the Blue: Phthalocyanines in Biomedical Optics," *Molecules* 17(1):98-144, 2012, published Dec. 23, 2011.

International Search Report dated Jul. 26, 2016 from International Application No. PCT/US2016/028113.

Written Opinion dated Jul. 26, 2016 from International Application No. PCT/US2016/028113.

International Search Report dated Apr. 11, 2019 from International Application No. PCT/US2018/55922 (5 pages).

Written Opinion dated Apr. 11, 2019 from International Application No. PCT/US2018/55922 (7 pages).

Japanese Notice of Reasons for Rejection dated Feb. 26, 2020 from corresponding Japanese Application No. 2017-555716 (with English-Language Translation).

* cited by examiner 24 hours after I.V. injection

"OFF-ON" "Always ON"

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa = D-Lys or D-Cys

<400> SEQUENCE: 1

Gln His Trp Ser Tyr Xaa Leu Arg Pro
1               5
```

-continued

```
<210> SEQ ID NO 2
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Pyroglutamic acid (Glp)
<220> FEATURE:
<221> NAME/KEY: MISC_FEATURE
<222> LOCATION: (6)..(6)
<223> OTHER INFORMATION: Xaa = D-Lys

<400> SEQUENCE: 2

Xaa His Trp Ser Tyr Xaa Leu Arg Pro Gly
1               5                   10


<210> SEQ ID NO 3
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Pyroglutamic acid (Glp)

<400> SEQUENCE: 3

Xaa His Trp Ser His Asp Trp Lys Pro Gly
1               5                   10
```

COMPOSITION COMPRISING A PHOTOSENSITIVE COMPOUND IN A POLYMERIC NANOPARTICLE, AND A METHOD OF USING THE COMPOSITION

CROSS REFERENCE TO RELATED APPLICATION

This is a U.S. continuation-in-part of International Application No. PCT/US2016/028113 filed on Apr. 18, 2016, which was published in English under PCT Article 21(2), which in turn claims the benefit of U.S. provisional patent application No. 62/150,125, filed on Apr. 20, 2015. Both applications are incorporated herein by reference in their entirety.

FIELD

This disclosure concerns compositions comprising a photosensitive compound and a polymeric nanoparticle, and a method of using the composition to treat diseases and conditions, including cancer.

BACKGROUND

Modalities for simultaneous therapy and diagnostics, known as theranostics, have gained significant interest for real-time biomedical imaging and site-specific treatment of the various diseases and conditions, including cancer. Phototherapy is a widely accepted non-invasive clinical approach to eradicate cancer, due in part, to the minimal side effects resulting from the selective illumination of the cancer site with light of an appropriate wavelength, while leaving healthy tissue untouched. When represented by photodynamic (PDT) and photothermal (PTT) therapies, the phototherapy requires light and a photosensitizer to generate reactive oxygen species and heat, respectively. The general procedure for PDT typically involves administration of non-toxic photoactive drugs (photosensitizers) which, upon exposure to light of specific wavelengths, damage cancer cells by producing reactive oxygen species (ROS). Unlike PDT, PTT does not require oxygen accessibility to damage targeted tissues, and by generating localized hyperthermia from absorbed light, PTT can be used to treat tissue that has a low oxygen concentration, such as low vascularized tumors.

For clinically relevant use, optical agents with absorption/emission in the near-infrared (NIR) window (about 650-900 nm) are advantageous because of the greater light penetration due to lower absorption and scatter from biological components. Therefore, there has been increased interest in the development and application of theranostic agents that can be activated by light with a wavelength in the NIR optical window. Body tissue is comparatively transparent in this spectral window, and so NIR light can be used for activation of photosensitizers accumulated in deep-seated cancer tumors without causing phototoxicity to normal, healthy tissue. Moreover, fluorescence imaging in the NIR optical window holds much promise due to minimal tissue autofluorescence and light scattering.

Due to their pronounced photophysical properties in the NIR range, the successful application of NIR dyes was reported in biomedical field, including for fluorescent imaging and phototherapy. Despite this interest, indocyanine green (ICG) is currently the only NIR dye FDA-approved as a clinical imaging agent. ICG has also been studied for PDT and PTT applications. However, low photostability in aqueous media resulting in a fast photodegradation, and quick clearance from the body significantly hampered the clinical application of ICG with respect to PDT and PTT, and thus hampered the possibility of ICG becoming a single theranostic agent in vivo.

SUMMARY

In view of the above, there is a need for a theranostic agent with good photostability in aqueous media. As PDT and PTT act via different mechanisms, their combination into the single therapeutic modality provides a highly efficient approach to treat neoplastic tissues. The addition of imaging abilities to such a combinatorial modality should result in a single highly effective theranostic nanomedicine platform. The availability of such a single agent-based platform with multiple functions would maximize efficiency of treatment outcome while diminishing the potential side effects on healthy organs and reducing time of treatment, effort and cost associated with application of separate imaging and therapeutic agents. Disclosed herein are embodiments of a composition that address this need. In some embodiments, the composition comprises a photosensitive compound and a polymer nanoparticle that encapsulates the photosensitive compound. The polymer nanoparticle may have a hydrophobic core, which encapsulates the photosensitizing compound, and/or may have a hydrophilic outer surface. The polymer may be a block copolymer and in some instances, is biodegradable and/or biocompatible. The polymer may comprise a polyethylene glycol moiety, and in some embodiments, the polymer is mPEG-b-PCL. In some instances, the polymer has an average molecular weight of from 10,000 Da to 20,000 Da, such as from 13,000 Da to 17,000 Da.

In some embodiments, the composition is a solution comprising a plurality of polymer nanoparticles, each polymer nanoparticle encapsulating at least one photosensitive compound. The solution may have a concentration of photosensitive compounds in the solution sufficient to quench a fluorescence emission associated with the photosensitive compounds. That is, the photosensitive compound may be loaded into the nanoparticle at a concentration sufficient to quench a fluorescence emission associated with the photosensitive compounds. The concentration may be sufficient that, after contacting a biological sample with the composition and exposing the sample to light, a fluorescence emission associated with the photosensitive compounds is produced. In other embodiments, the concentration of photosensitive compound in the nanoparticle is sufficient that a fluorescence emission associated with the photosensitive compound can be detected before the biological sample is contacted by the solution. That is, the concentration is sufficient to prevent the self-quenching before contacting the biological sample. In some embodiments, the concentration is from 0.01 mg/mL to 2 mg/mL, such as from 0.03 mg/mL to 1 mg/mL, or from 0.05 mg/mL to 0.8 mg/mL. In some embodiments, the concentration is from 0.01 mg/mL to less than 0.4 mg/mL, such as from 0.01 mg/mL to 0.4 mg/mL or less, from 0.05 mg/mL to 0.3 mg/mL and may produce a highly fluorescent formulation prior to contacting the biological sample. The nanoparticle may have a loading efficiency of from greater than zero to 4%, such as from 2% to 3.5%.

In other embodiments, the concentration is from 0.4 mg/mL to 2 mg/mL or greater, such as from 0.4 mg/mL to 1 mg/mL, from 0.4 mg/mL to 0.75 mg/mL, or from 0.4 mg/mL to 0.6 mg/mL, and may result in an OFF/ON formulation, where the solution does not produce a fluorescence emission associated with the photosensitive compound until the composition contacts the biological sample. The nanoparticle may have a loading efficiency of from 4% to 8%, such as from 4.5% to 8%.

In some embodiments, the photosensitive compound is a compound that, after contacting a biological sample with the composition and exposing the sample to light, produces a fluorescence emission, reactive oxygen species, heat or any combination thereof. The biological sample may be a cell or a tissue sample. The light may have a wavelength of from 650 nm to 900 nm. In particular embodiments, the composition produces a fluorescence emission, reactive oxygen species and heat.

In some embodiments, the photosensitive compound is a phthalocyanine or a phthalocyanine derivative having a formula

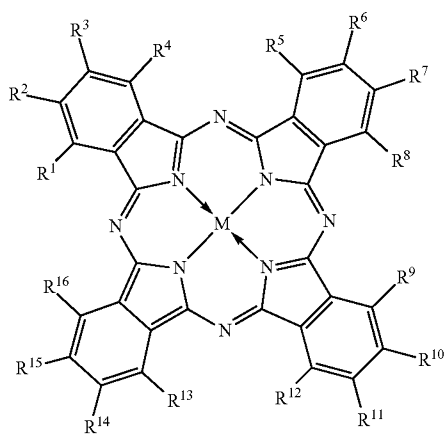

wherein $R^1$-$R^{16}$ are independently selected from hydrogen, halogen, $NO_2$, cyano, amino, aminocarbonyl, aminosulfonyl, carboxyl, carboxyl ester, aliphatic, heteroaliphatic, aryl, aryloxy, arylthio, heteroaryl, heteroaryloxy or heteroarylthio, or any two adjacent R groups together form an aryl, heteroaryl, cycloalkyl or heterocycloalkyl ring, and M is a metal, metalloid, substituted metal or substituted metalloid. In particular embodiments, the compound has a formula

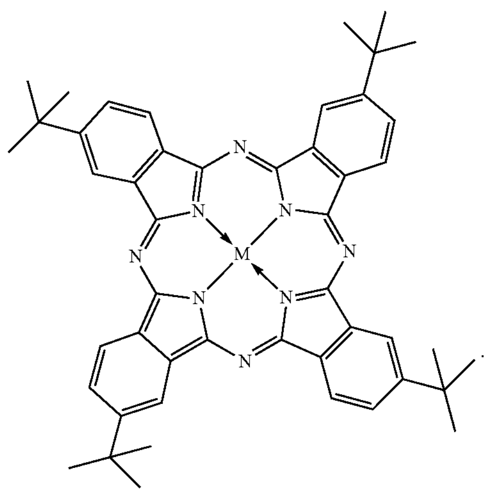

In other embodiments, the phthalocyanine derivative is a naphthalocyanine having a formula

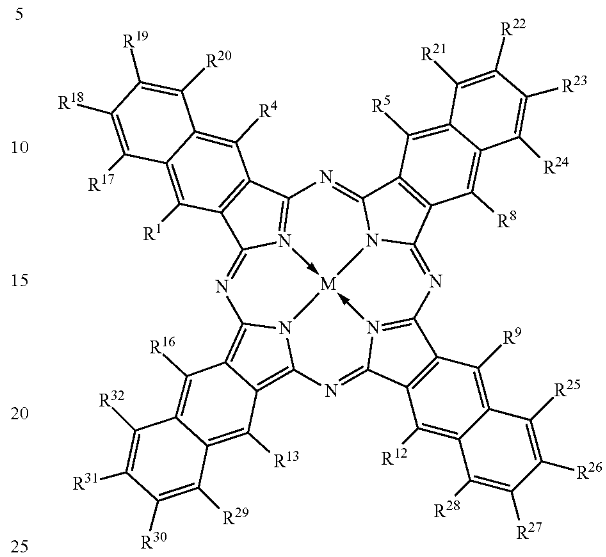

Wherein M, $R^1$, $R^4$, $R^5$, $R^8$, $R^9$, $R^{12}$, $R^{13}$ and $R^{16}$ are as defined above, and $R^{17}$-$R^{32}$ are selected from hydrogen, halogen, $NO_2$, cyano, amino, aminocarbonyl, aminosulfonyl, carboxyl, carboxyl ester, aliphatic, heteroaliphatic, aryl, aryloxy, arylthio, heteroaryl, heteroaryloxy or heteroarylthio, or any two adjacent R groups together form an aryl, heteroaryl, cycloalkyl or heterocycloalkyl ring. In particular instances, $R^1$, $R^4$, $R^5$, $R^8$, $R^9$, $R^{12}$, $R^{13}$ and $R^{16}$-$R^{32}$ are hydrogen.

In some embodiments of the above formulas, M is a substituted metal or substituted metalloid. In certain embodiments, M is a substituted silicon or a substituted aluminum. In some embodiments, the silicon or aluminum may be substituted with one or more of —OH, aliphatic, or heteroaliphatic, such as one or more of —OH, $C_{2-10}$alkyl, —O—$C_{2-10}$ alkyl, —O—Si($C_{2-10}$alkyl)$_3$, —O—C(O)—$C_{2-10}$ alkyl, or —O—C(O)($CH_2$)$_{2-6}$$CO_2$($C_{2-6}$ alkyl), where each alkyl optionally may be further substituted as defined herein. In certain embodiments, M is $Si(OH)_2$ substituted with one or more hydrophobic groups. In certain instances, M is silicon bis(trihexylsilyloxide), hydroxysilyl methyl succinate silicon dioctyloxide, or dimethyl O,O'-silanediyl disuccinate. In other embodiments, M is Al substituted with —O—C(O)-unsubstituted alkyl or —O—C(O)-substituted alkyl, such as —O—C(O)-unsubstituted $C_{2-10}$alkyl or —O—C(O)-substituted $C_{2-10}$alkyl.

In particular embodiments, the photosensitive compound is

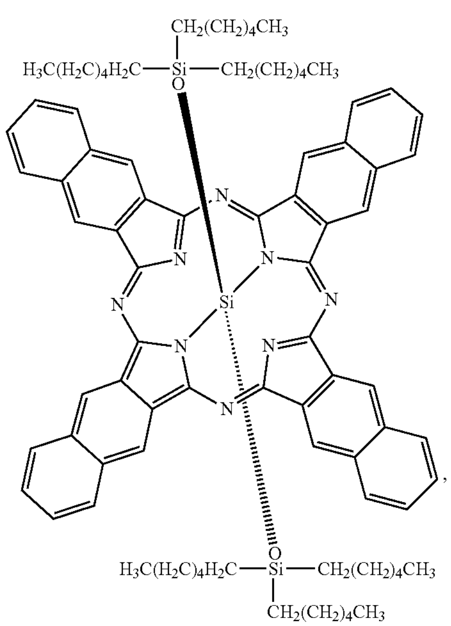

and the composition may further comprise an mPEG-b-PCL polymer with an average molecular weight of about 15,000 Da.

The composition may comprise a second photosensitive compound, which may be the same or different from the photosensitive compound. In some embodiments, the composition further comprises a targeting moiety. The targeting moiety may be a cancer targeting moiety, such as a solid tumor cancer targeting moiety, and in some instances, the targeting moiety is LHRH protein.

A pharmaceutical preparation, comprising the composition and a pharmaceutically acceptable excipient, is also disclosed.

Additionally, disclosed herein are embodiments of a method of using the composition, comprising contacting a biological cell with the composition, and exposing the cell and the composition to light. In some embodiments, exposing the cell and the composition to light comprises exposing the cell and composition to light of a sufficient wavelength for a sufficient length of time to cause the composition to produce a fluorescent emission, generate radical oxygen species, generate heat, or any combination thereof. In other embodiments, exposing the cell and the composition to light comprises exposing the cell and composition to light of a sufficient wavelength for a sufficient length of time to cause the composition to kill the cell by producing radical oxygen species, generating heat or a combination thereof. Exposing the cell and composition to light of a sufficient wavelength may comprise exposing the cell and composition to light having a wavelength from 650 nm to 900 nm. In certain embodiments, contacting the biological cell with the composition comprises contacting the biological cell with a solution comprising a plurality of polymer nanoparticles, each polymer nanoparticle encapsulating at least one photosensitive compound, and the solution having a concentration of photosensitive compounds sufficient to produce high fluorescence (such as a fluorescence quantum yield ($\Phi_F$) of greater than about 10%, such as from 10% to 20% or greater, from 10% to 15%, or from 10% to 13%), or alternatively quench a fluorescence emission associated with the photosensitive compounds before the solution contacts the biological cell. The concentration also may be sufficient to produce a fluorescence emission associated with the photosensitive compounds after the solution contacts the biological cell and is exposed to the light. In some embodiments, the method further comprises detecting the fluorescent emission.

The cell may be a cancer cell, and may be located in a subject. In some instances contacting the biological cell with the composition comprises administering the composition to the subject, such as by intravenous, intraperitoneally, or topical route, or by direct injection into a tumor.

Also disclosed herein is a method of making the composition, comprising dissolving a polymer and a photosensitive compound in a solvent to form a solution, adding water rapidly to the solution to form an emulsion or nanodispersion, and evaporating the solvent without external heating to form monodispersed polymer nanoparticles. The solvent may be THF. In some embodiments, method further comprises selecting a ratio of an amount of polymer to an amount of photosensitive compound to provide a desired loading of photosensitive compound in the polymer nanoparticles.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SEQUENCE LISTING

Figure 1:
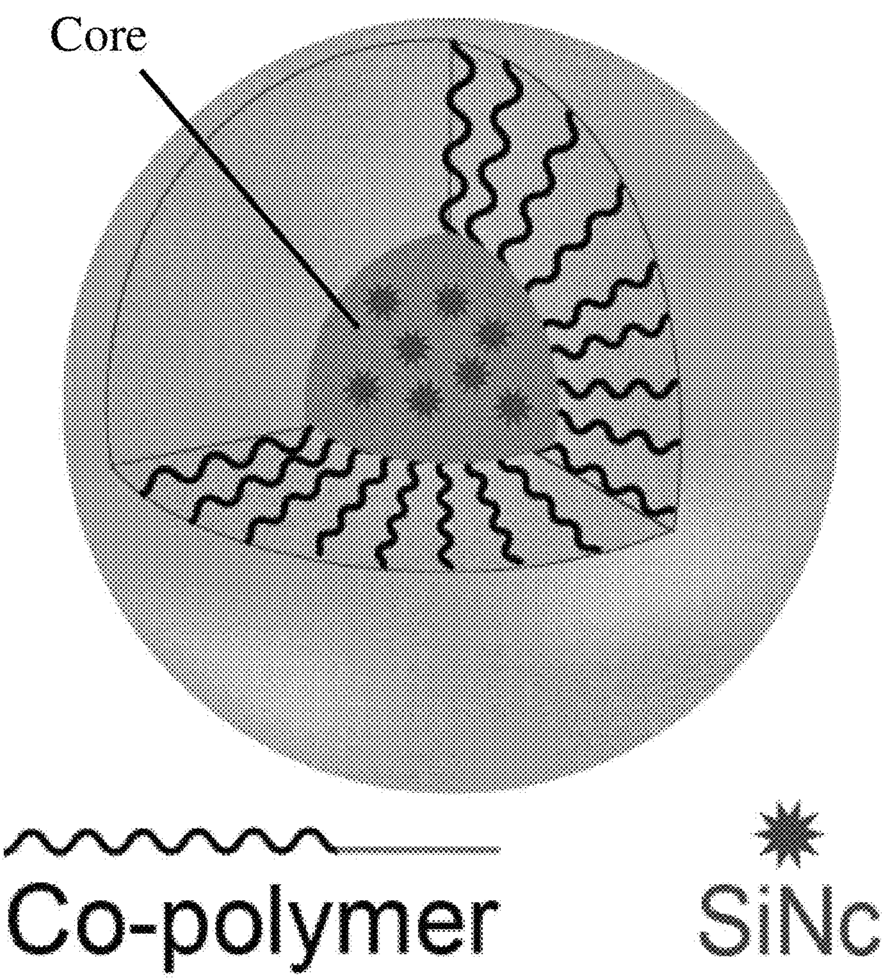
FIG. 1 is a schematic diagram of an exemplary embodiment of a composition disclosed herein, illustrating phthalocyanines encapsulated in the core of the polymer nanoparticle.

The amino acid sequences listed in the accompanying sequence listing are shown using standard three letter code for amino acids, as defined in 37 C.F.R. 1.822. The Sequence Listing is submitted as an ASCII text file, created on Oct. 16, 2017, 1.2 KB, which is incorporated by reference herein.

DETAILED DESCRIPTION

I. Definitions

The following explanations of terms and methods are provided to better describe the present disclosure and to guide those of ordinary skill in the art in the practice of the present disclosure. The singular forms “a,” “an,” and “the” refer to one or more than one, unless the context clearly dictates otherwise. The term “or” refers to a single element of stated alternative elements or a combination of two or more elements, unless the context clearly indicates otherwise. As used herein, “comprises” means “includes.” Thus, “comprising A or B,” means “including A, B, or A and B,” without excluding additional elements.

Unless otherwise indicated, all numbers expressing quantities of components, molecular weights, percentages, temperatures, times, and so forth, as used in the specification or claims are to be understood as being modified by the term “about.” Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word “about” is recited.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

"Aliphatic" refers to a substantially hydrocarbon-based compound, group or moiety (e.g., $C_6H_{13}$, for a hexane moiety), including alkanes, alkenes, alkynes, including cyclic versions thereof, such as alkyl, alkenyl, alkynyl, cycloalkyl, cycloalkenyl, and cycloalkynyl, and further including straight- and branched-chain arrangements, and all stereo and position isomers as well. Unless expressly stated otherwise, an aliphatic group contains from one to at least twenty-five carbon atoms ($C_1$-$C_{25}$); for example, from one to fifteen ($C_1$-$C_{15}$), from one to ten ($C_1$-$C_{10}$), from one to six ($C_1$-$C_6$), or from one to four ($C_1$-$C_4$) carbon atoms. A cycloaliphatic group, such as cycloalkyl, contains at least three carbon atoms, such as from three to at least 25 carbon atoms. The term "lower aliphatic" refers to an aliphatic group comprising from one to ten carbon atoms. An aliphatic chain may be substituted or unsubstituted. Unless expressly referred to as an "unsubstituted aliphatic," an aliphatic group can either be unsubstituted or substituted.

"Alkyl" refers to a straight (i.e., unbranched) or branched saturated hydrocarbon chain. Unless expressly stated otherwise, an alkyl group contains from one to at least twenty-five carbon atoms ($C_1$-$C_{25}$); for example, from one to fifteen ($C_1$-$C_{15}$), from one to ten ($C_1$-$C_{10}$), from one to six ($C_1$-$C_6$), or from one to four ($C_1$-$C_4$) carbon atoms. Examples of alkyl groups include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkoxy" refers to the group —O-alkyl.

"Alkylthio" refers to the group —S-alkyl.

"Amino" refers to the group —NR'R", wherein R' and R" independently are selected from hydrogen, aliphatic, or heteroaliphatic, or where R' and R" are optionally joined together with the nitrogen bound thereto to form a cycloamino group such as a heterocyclic or heteroaryl group comprising at least one ring nitrogen. Exemplary cycloamino groups include, but are not limited to, pyrrolidine, pyrrole, imidazole, triazole, tetrazole, piperidine, triazinane, piperazine, morpholine, azepane, diazepane, azocane, diazocane, azonane or azecane.

"Aminocarbonyl" refers to a chemical functional group —C(=O)-amino, where amino is as defined herein. A primary aminocarbonyl is $—CONH_2$.

"Cyano" refers to the chemical functional group —CN.

"Carboxyl," "carboxylic acid" or "carboxy" refers to the chemical functional group $—CO_2H$.

"Carboxyl ester," "carboxylic acid ester," or "carboxy ester" refers to the chemical functional group $—CO_2R$ where R is aliphatic, heteroaliphatic, aryl or heteroaryl.

"Carboxylate" refers to a $—CO_2^-$ or $—CO_2—$ moiety. For example, a metal may be substituted with an alkyl carboxylate moiety, such as $C_{1-10}alkylCO_2—$.

"Aminosulfonyl" refers to a chemical function group $—SO_2$-amino, where amino is as defined herein. A primary aminosulfonyl is $—SO_2NH_2$.

"Acyl" means, unless otherwise stated, —C(O)R where R is H, aliphatic, heteroaliphatic, aryl or heteroaryl.

"Aryl" or "Ar" refers to a monovalent aromatic carbocyclic group of from 6 to 15 carbon atoms having a single ring (e.g., phenyl) or multiple condensed rings (e.g., naphthyl or anthryl) in which at least one of the condensed rings is aromatic (e.g., 2-benzoxazolinone, 9,10-dihydrophenanthrene, and the like), provided that the point of attachment is through an atom of the aromatic aryl group. Unless otherwise specified, the aryl group may be optionally substituted. Preferred aryl groups include phenyl and naphthyl.

"Aryloxy" refers to the group —O-aryl.

"Arylthio" refers to the group —S-aryl.

"Heteroaliphatic" refers to an aliphatic compound, moiety, or group having at least one heteroatom, i.e., one or more carbon atoms has been replaced with an atom having at least one lone pair of electrons, typically nitrogen, oxygen, phosphorus, silicon, or sulfur. Typically, a heteroaliphatic group contains from two to at least twenty-five carbon or heteroatoms (referred to as a $C_2$-$C_{25}$ heteroaliphatic although at least one of the carbon atoms has been replaced by a heteroatom); for example, from two to fifteen ($C_2$-$C_{15}$), from two to ten ($C_2$-$C_{10}$), from two to six (C2-C6), or from two to four carbon or heteroatoms ($C_2$-$C_4$). Heteroaliphatic compounds or groups may be substituted or unsubstituted, branched or unbranched, cyclic or acyclic, and include "alkoxy", "alkylthio", "heterocycle", "heterocyclyl", "heterocycloaliphatic", or "heterocyclic" groups. A heterocyclic group contains at least three atoms, such as from three to at least twenty five, referred to as $C_3$-$C_{25}$ (although at least one of the carbon atoms has been replaced by a heteroatom). Examples of heteroaliphatic groups include methoxy; ethoxy; propoxy; butoxy; aliphatic carboxylate, such as alkyl carboxylate, including, but not limited to, $OC(O)(CH_2)_2CO_2CH_3$ or $—OC(O)C_{2-10}alkyl$; and $OSi(C_6H_{13})_3$. Examples of heterocycles include morpholine and piperidine.

"Halo", "halide" or "halogen" refers to fluoro, chloro, bromo, and iodo.

"Heteroaryl" refers to an aromatic group having from 5-15 ring atoms, including from 1 to 15 carbon atoms and at least one, and more typically 1 to 4, heteroatoms selected from oxygen, nitrogen or sulfur within the ring. Unless otherwise specified, the heteroaryl group may be optionally substituted. Such heteroaryl groups can have a single ring (e.g., pyridinyl, imidazolyl or furyl) or multiple condensed rings (e.g., indolizinyl, quinolinyl, benzimidazolyl, benzopyrazolyl or benzothienyl), wherein at least one of the condensed rings is aromatic and may or may not contain a heteroatom, provided that the point of attachment is through an atom of an aromatic ring. In one embodiment, the nitrogen and/or sulfur ring atom(s) of the heteroaryl group are optionally oxidized to provide N-oxide (N→O), sulfinyl, or sulfonyl moieties. Preferred heteroaryls include pyridinyl, pyrrolyl, indolyl, thiophenyl, benzopyrazolyl and furanyl.

"Heteroaryloxy" refers to the group —O-heteroaryl.

"Heteroarylthio" refers to the group —S-heteroaryl.

As used herein, the term "phthalocyanines" refers to phthalocyanine and phthalocyanine derivatives, including naphthalocyanine.

As used herein, a group can be substituted with one or more substituents (up to two substituents for each methylene [$—CH_2—$] carbon, such as in an saturated aliphatic chain, or up to one substituent for each carbon of a —C=C— double bond such as in an aryl group or an unsaturated aliphatic chain, or up to one substituent for a carbon of a terminal methine group). Exemplary substituents include, but are not limited to, amino, amide, sulfonamide, halo, cyano, carboxy, carboxy ester, hydroxyl, oxo (=O), mercapto, trifluoromethyl, alkyl, alkoxy, alkylthio, thioalkoxy, arylalkyl, heteroaryl, alkylamino, dialkylamino, aryl, aryloxy, heteroaryloxy, heterocyclic, arylthio, heteroarylthio or other functionality. In a preferred embodiment, a group that is substituted has 1 substituent, 1 or 2 substituents, 1, 2, or 3 substituents or 1, 2, 3 or 4 substituents.

Also, it is understood that the above definitions are not intended to include impermissible substitution patterns. Such impermissible substitution patterns are understood by a person having ordinary skill in the art.

Additionally, it is understood by a person of ordinary skill in the art that if an atom does not appear to have sufficient specific bonds to satisfy valence requirements, such as an apparent trivalent carbon, there are sufficient implicit hydrogens present to satisfy those valence requirements.

"Hydrophobic" refers to a group or moiety that substantially does not attract water. Hydrophobic groups typically are non-polar. A hydrophobic group or moiety increases the hydrophobicity of the molecule, as determined by the octanol/water partition coefficient. Exemplary hydrophobic groups include, but are not limited to, alkyl groups, alkyl esters, aryl groups, halogenated alkyl groups and alkoxy groups attached to a metal or metalloid at the oxygen.

"Metalloid" refers to a chemical element that has properties in between those of a metal and a non-metal. Example metalloid elements include boron, silicon, germanium, arsenic, antimony and tellurium.

The terms "administer," "administering," "administration," and the like, as used herein, refer to methods that may be used to enable delivery of compositions to the desired site of biological action. These methods include, but are not limited to, intraarticular (in the joints), intravenous (i.v.), intramuscular, intratumoral, intradermal, intraperitoneal, subcutaneous, orally, topically, intrathecally, inhalationally, transdermally, rectally, direct injection into a tumor, and the like. Administration techniques that can be employed with the agents and methods described herein are found in e.g., Goodman and Gilman, The Pharmacological Basis of Therapeutics, current ed.; Pergamon; and Remington's, Pharmaceutical Sciences (current edition), Mack Publishing Co., Easton, Pa.

"Pharmaceutically acceptable excipient" and "pharmaceutically acceptable carrier" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

"Preparation" is intended to include formulations of an active compound or composition with another material, such as a pharmaceutically acceptable excipient and/or an encapsulating material as a carrier to provide a capsule. Similarly, cachets and lozenges are included. Tablets, powders, capsules, pills, cachets, and lozenges can be used as solid dosage forms suitable for oral administration. Preparations suitable for administration by injection may include solutions, suspensions, and emulsions. Preparations suitable for topical administration may include creams, solutions, suspensions, pastes and the like.

"Therapeutically effective amount" or "effective amount" refers to a sufficient amount of at least one agent being administered to achieve a desired result, e.g., to relieve to some extent one or more symptoms of a disease or condition being treated, or to effectively image a location or tumor in a patient, or in an in vitro assay. In certain instances, the result is a reduction and/or alleviation of the signs, symptoms, or causes of a disease or condition, or any other desired alteration of a biological system. In certain instances, an "effective amount" for therapeutic uses is the amount of the composition or preparation comprising an agent as disclosed herein required to provide a clinically significant decrease in a disease. An appropriate "effective amount" in any individual case can be determined using any suitable technique, such as a dose escalation study.

II. Overview

Despite advances in chemotherapeutic and pharmaceutical approaches, surgery remains the cornerstone of modern cancer treatment. Currently, only surgically removing most malignant tissues can reduce cancer recurrence, and significantly improve patient survival. However, the success of any cancer surgery is limited by the surgeon's ability to visually differentiate between tumor and normal tissue. Even with the best microsurgical technique, surgeons leave behind residual microscopic tumors, eventually leading to cancer relapse. If these tumors could be detected, resected and/or treated more efficiently during surgery, survival rates would significantly increase. It is important, therefore, to improve tumor delineation during surgery for enhancing its surgical resection efficiency and provide an effective intraoperative treatment, to further eliminate any un-resectable tumors. A technology that overcomes the problems related to a surgeon's ability to visually detect malignant tissue and achieve maximum surgical resection further enhanced by intraoperative therapy would provide a significant advance in cancer treatment and have strong commercial potential.

To meet the current medical needs, disclosed herein are embodiments of a composition and formulation that can enable maximal surgical resection by real-time optically imaging of cancer tumors during surgery, and, at the same time, can be also employed intraoperatively to mediate a safe phototherapy for eradicating hidden and/or un-resectable tumors.

Unlike intraoperative radiotherapy or adjuvant chemotherapy, phototherapy (including photodynamic therapy (PDT) and photothermal therapy (PTT)) is characterized by minimal side effects because it selectively kills cancer cells using a non-toxic photoactive drug (photosensitizer), specifically activated by targeted light. In PDT, cytotoxic reactive oxygen species (ROS) are generated by a photosensitizer accumulated in the cancer cells upon light illumination of a specific wavelength. Unlike for PDT, PTT agents absorb the light and convert it into heat, which is then transferred to the intracellular environment, generating localized hyperthermia. Therefore, phototherapy offers higher therapeutic selectivity for cancer cells and lower toxicity towards healthy tissue. As PDT and PTT act against cells via different mechanisms, their combination into the single therapeutic modality provides a highly efficient tactic to treat cancer tumors intraoperatively, including solid tumors such as ovarian and breast cancer tumors, and skin melanomas. Such a dual therapeutic ability of the composition via different mechanisms significantly reduces the probability of the cells developing therapy resistance. Additionally, the developed multifunctional formulation as a single therapeutic modality avoids multiple administrations of different therapeutic agents and thus may improve patient compliance.

One of the major challenges in the clinical application of PDT and PTT as well as fluorescence optical imaging is that the visible light required to activate the appropriate agents can only penetrate through several millimeters of tissue. Moreover, fluorescence imaging in the NIR optical window holds much promise due to minimal tissue autofluorescence and light scattering. In some embodiments, the disclosed composition exhibits strong absorbance in the NIR region, which is a transparency window for biological tissues. Additionally, the disclosed compositions can easily be detected via optical imaging and efficiently transfer the absorbed NIR optical energy into ROS and heat. Upon exposure to NIR light, the composition as a single photoactive agent simultaneously (1) generates a strong fluorescence signal inside cancer cells, as required for image-guided surgery, and (2) produces both toxic ROS for photodynamic therapy (PDT) and heat, that can lead to hyperthermia in the cells, for specific and efficient destruction of the cancer cells. Since biological tissue absorbs and scatters light the least in this range, NIR light used for activation of this agent is useful for imaging and treatment of deep-seated tumors.

Compositions disclosed herein provide a theranostic nanomedicinal modality that enables both imaging and maximal treatment of un-resected and chemo-resistant cancer cells, for example ovarian cancer cells, using an intraoperative multimodal phototherapy. Thus, following the accumulation of the developed agent in tumor tissue by monitoring the fluorescence emission of the photosensitizer after systemic administration, phototherapy can be precisely applied to a detected region by selectively illuminating the cancer tissue with light of an appropriate wavelength, while leaving health organs untouched. The developed composition as single agent-based platform with multiple functions will maximize efficiency of treatment outcome, while diminishing the potential side effects on healthy organs and reducing manufacturing costs associated with application of two separate imaging and therapeutic agents. The synergistic effect of the combined noninvasive photodynamic (PDT) and photothermal (PTT) therapy will improve the therapeutic efficiency, overcome multidrug resistance and decrease the dosage-limiting toxicity of current chemotherapy drugs. The disclosed composition can also be used in combination with chemotherapy and/or radiation therapy for the treatment of certain other diseases besides cancer.

III. Compositions

A. Compounds

Disclosed herein are embodiments of a composition comprising a photosensitizing agent suitable for PDT, PTT and/or fluorescence imaging, and a polymeric nanoparticle.

In some embodiments, the photosensitizing agent is a phthalocyanine. Certain disclosed embodiments have formula I

I

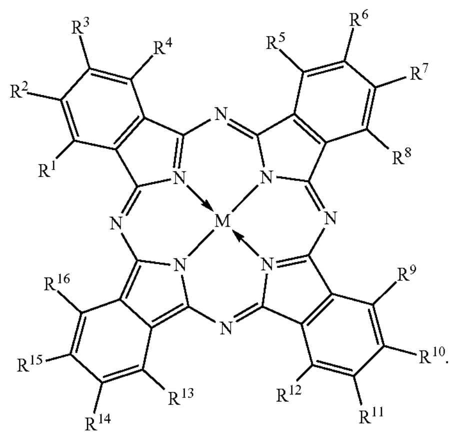

With reference to formula I, $R^1$-$R^{16}$ are independently selected from hydrogen, halogen, $NO_2$, cyano, amino, aminocarbonyl, aminosulfonyl, carboxyl, carboxyl ester, aliphatic, heteroaliphatic, aryl, aryloxy, arylthio, heteroaryl, heteroaryloxy, or heteroarylthio, or any two adjacent R groups together form an aryl, heteroaryl, cycloalkyl or heterocycloalkyl ring, and M is a metal, metalloid, substituted metal or substituted metalloid. In some embodiments, the substituted metal or substituted metalloid is a metal or metalloid substituted with one or more hydrophobic substituents and/or one or more substituents that inhibit aggregation of the phthalocyanines. In particular embodiments, M is substituted Si or substituted Al, where the Si or Al is substituted with one or more hydrophobic groups, as defined herein. Suitable substituents for the substituted metal or substituted metalloid, such as Si or Al, include, but are not limited to, H; OH; halogen, such as F, Cl, Br, and I; aliphatic, such as alkyl; heteroaliphatic, such as alkoxy, or alkyl carboxylate; amino; aryl; or heteroaryl.

In certain embodiments, $R^1$-$R^{16}$ are independently hydrogen or aliphatic. In particular embodiments, $R^1$-$R^{16}$ are hydrogen; $R^2$, $R^6$, $R^{10}$ and $R^{14}$ are tert-butyl and the rest are hydrogen; $R^1$, $R^4$, $R^5$, $R^8$, $R^9$, $R^{12}$, $R^{13}$ and $R^{16}$ are butoxy and the rest are hydrogen; or $R^2$, $R^3$, $R^6$, $R^7$, $R^{10}$, $R^{11}$, $R^{14}$ and $R^{15}$ are octyloxy and the rest are hydrogen.

In other embodiments, $R^2$ and $R^3$, $R^6$ and $R^7$, $R^{10}$ and $R^{11}$ and $R^{14}$ and $R^{15}$ together form aryl rings, leading to phthalocyanine derivatives, or naphthalocyanines (Nc), having formula II

II

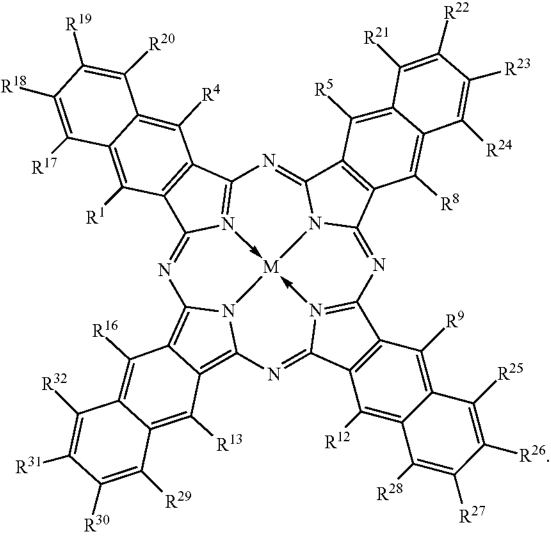

With reference to formula II, $R^{17}$-$R^{32}$ are as defined for $R^1$-$R^{16}$ above.

In some embodiments of formula II, $R^1$, $R^4$, $R^5$, $R^8$, $R^9$, $R^{12}$, $R^{13}$ and $R^{16}$-$R^{32}$ are hydrogen. In other embodiments, $R^{19}$, $R^{22}$, $R^{26}$, and $R^{30}$ are tert-butyl and the rest are hydrogen; or $R^1$, $R^4$, $R^5$, $R^8$, $R^9$, $R^{12}$, $R^{13}$ and $R^{16}$ are butoxy and the rest are hydrogen.

In some embodiments of formulas I and II, M is or comprises silicon. In some embodiments, the silicon is substituted, and in particular embodiments, the silicon is substituted with OH, CN, aliphatic, heteroaliphatic, aryl, heteroaryl, alkoxy, aryloxy, heteroaryloxy, alkylthio, arylthio, heteroarylthio, acyl, halo, or a combination thereof. The substituent may be further substituted as disclosed herein. In alternative embodiments, M is or comprises aluminum. In some embodiments, the aluminum is substituted, and in particular embodiments, the aluminum is substituted with OH, CN, aliphatic, heteroaliphatic, aryl, heteroaryl, alkoxy, aryloxy, heteroaryloxy, alkylthio, arylthio, heteroarylthio, acyl, halo, or a combination thereof. The substituent may be further substituted as disclosed herein. In some embodiments, the metal or metalloid is substituted with a hydrophobic group or moiety. That is, the substitution of the metal or metalloid, such as silicon or aluminum, increases hydrophobicity of the molecule, as determined by the octanol/water partition coefficient. Without being bound to a particular theory, increasing hydrophobicity of the photosensitizing agent may help to increase the molecule's solubility in organic solvents and/or increase its loading in to the polymer nanoparticle. In some embodiments, the substitution inhibits the aggregation of the photosensitive compound molecules.

In particular embodiments, the silicon or aluminum may be substituted with one or more of —OH, aliphatic, or heteroaliphatic, such as one or more of —OH, $C_{2-10}$alkyl, —O—$C_{2-10}$alkyl, —O—Si($C_{2-10}$alkyl)$_3$, —O—C(O)—$C_{2-10}$alkyl, or —O—C(O)$(CH_2)_{2-6}CO_2$($C_{2-6}$alkyl), where each alkyl optionally may be further substituted as defined herein. In certain embodiments, M is $Si(OH)_2$ substituted with one or more hydrophobic groups. In certain instances, M is silicon bis(trihexylsilyloxide), hydroxysilyl methyl succinate silicon dioctyloxide, or dimethyl O,O'-silanediyl disuccinate. In other embodiments, M is Al substituted with —O—C(O)H, —O—C(O)-unsubstituted alkyl, or —O—C(O)-substituted alkyl, such as —O—C(O)H, —O—C(O)-unsubstituted $C_{2-10}$alkyl, or —O—C(O)-substituted $C_{2-10}$alkyl.

In some embodiments, M is $Si(OH)_2$. In other embodiments, M is silicon substituted with OH, $OC(O)(CH_2)_2CO_2CH_3$, trihexylsilyloxide($OSi(C_6H_{13})_3$), or combinations thereof.

Exemplary embodiments of compounds having formula I include

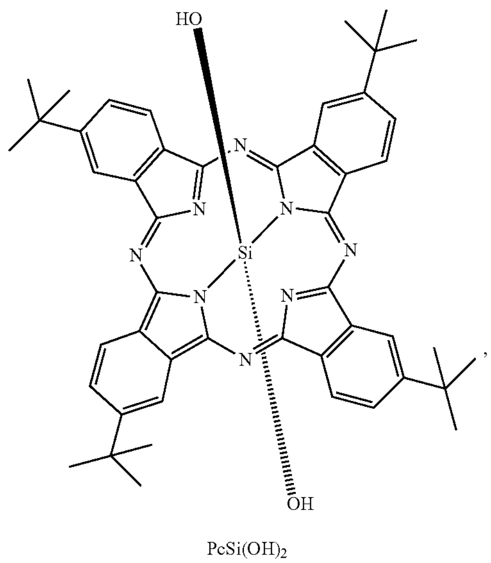

$PcSi(OH)_2$

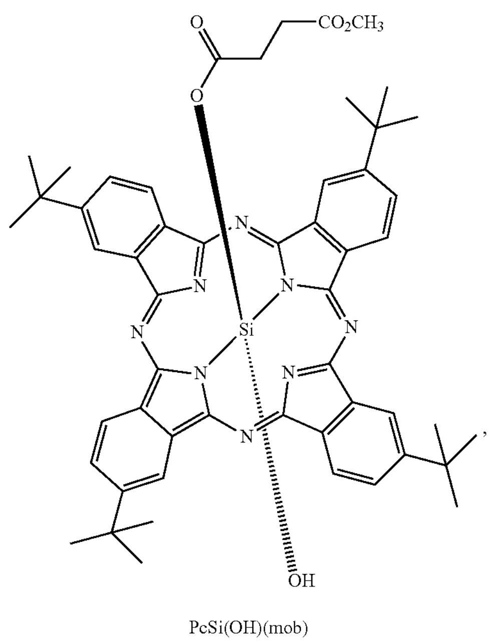

PcSi(OH)(mob)

-continued
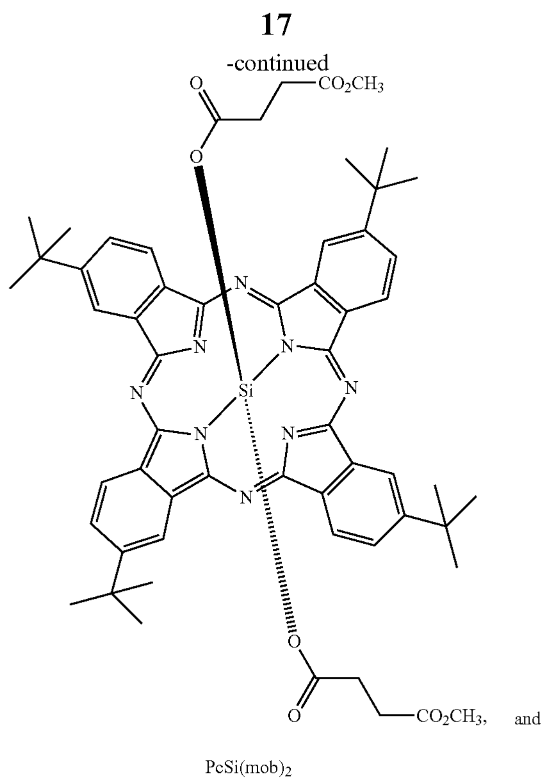
and
$PcSi(mob)_2$
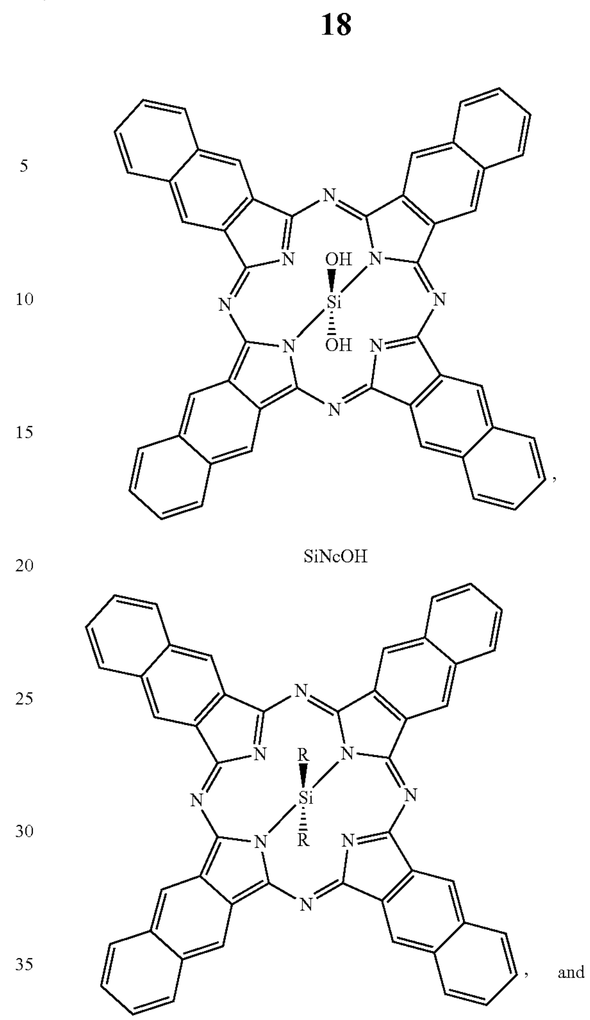
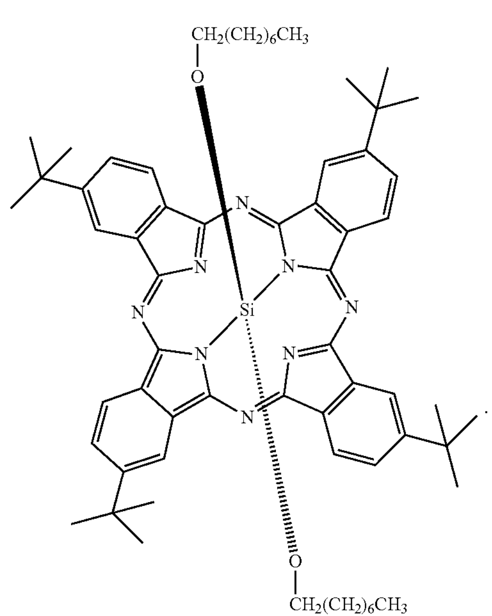
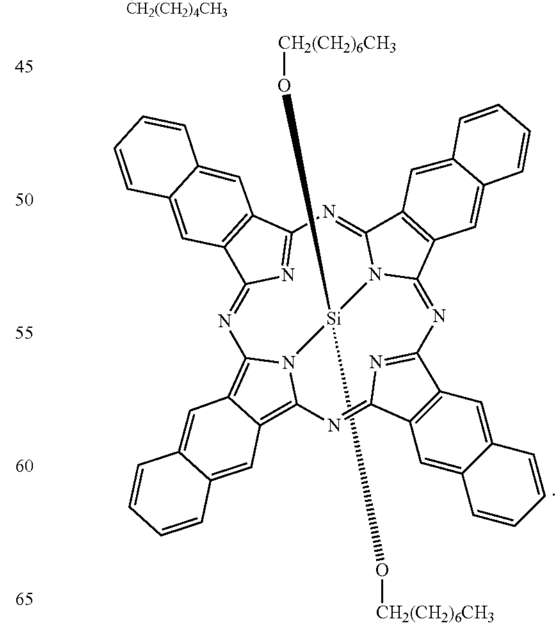
Exemplary embodiments of compounds having formula II include Other exemplary embodiments include

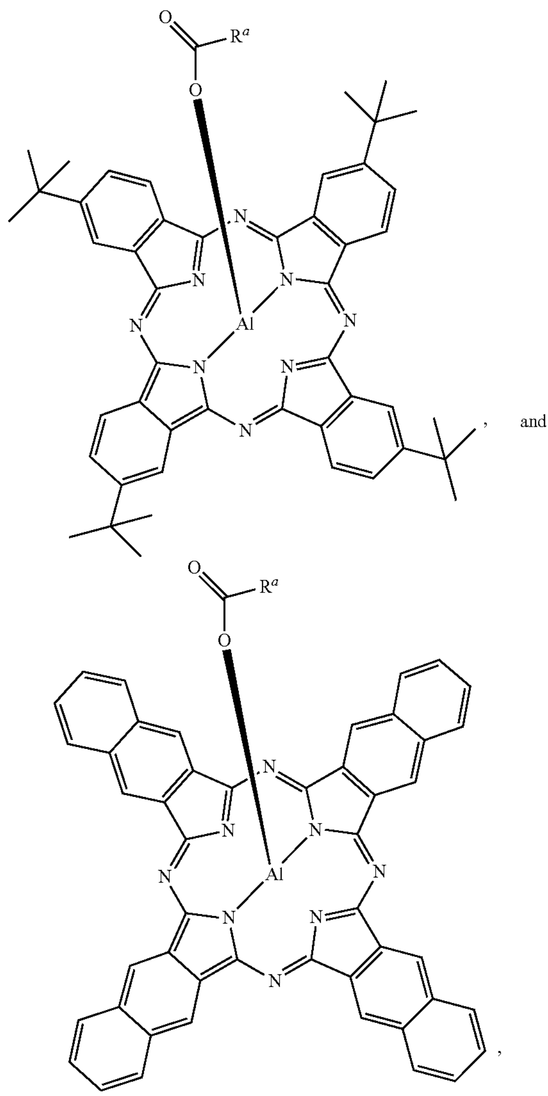

where $R^a$ is H, or optionally substituted alkyl, and in some embodiments, $R^a$ is H, unsubstituted $C_{1-10}$alkyl, or substituted $C_{1-10}$alkyl. In certain embodiments, $R^a$ is H, $C_{2-10}$alkyl, or $C_{2-10}$alkyl substituted with carboxyl ester, carboxyl, oxo, CN, OH, or amino.

B. Polymers

Phthalocyanines (Pc), including phthalocyanine derivatives such as naphthalocyanine, have significant potential as theranostic agents due to strong absorption of the far-red and NIR light. These photosensitizers generally have large conjugated domains resulting in strong energy absorption and thus high fluorescence quantum yield, needed for efficient PDT and fluorescence imaging. Additionally, phthalocyanines generate heat suitable for PTT. However, due to their planar structures, the molecules have a tendency to aggregate in aqueous medium through π-π stacking and hydrophobic interactions, resulting in the self-quenching effect of their excited state. The described behavior of phthalocyanines significantly decreases the photodynamic effect and imaging abilities after their systemic administration. Furthermore, clinical application of phthalocyanines suffers considerably from their poor water solubility and limited selectivity for cancer cells.

One approach to both prevent or reduce aggregation of the phthalocyanines, and improve their water solubility and selectivity, is to encapsulate the phthalocyanines in a particle, such as a nanoparticle. Suitable nanoparticles include nanoparticles that encapsulate phthalocyanines, and/or improve their water solubility. In some embodiments, the nanoparticles substantially prevent phthalocyanine aggregation. In other embodiments, the nanoparticles reduce phthalocyanine aggregation compared to phthalocyanine aggregation in a phthalocyanine solution without polymer nanoparticles and with a similar phthalocyanine concentration. In some embodiments, the polymer nanoparticle is a biodegradable polymer nanoparticle, that is a polymer nanoparticle capable of being decomposed by bacteria or other living organisms, such as a patient or subject who is administered the polymer nanoparticle. And/or the polymer nanoparticle may be biocompatible, that is substantially non-toxic to a patient, and upon administration, does not result in a substantial immune response.

The polymer may be selected for its compatibility with a particular phthalocyanine or phthalocyanine derivative, including naphthalocyanine. In some embodiments, the polymer is selected such that the solubility parameters of the polymer or polymer nanoparticle and phthalocyanine or phthalocyanine derivative are similar. In some embodiments, solubility parameters of the polymer or polymer nanoparticle and phthalocyanine or derivative thereof, including naphthalocyanine, are from within 25% of each other to substantially the same as each other, advantageously from within 20% of each other to substantially the same as each other. Solubility parameters can be calculated by standard method known to a person of ordinary skill in the art. Additional information concerning calculating solubility parameters can be found in Fedors, R. F., *JPL Quarterly Technical Review*, Vol. 3 (1):45-53, which is incorporated herein by reference.

The polymer may be a block copolymer. At least one monomer of the copolymer may be selected to enhance or improve the water solubility of the polymer nanoparticle, and/or at least one monomer of the copolymer may be selected to provide an environment in the polymer nanoparticle suitable for encapsulating photosensitive compounds, such as phthalocyanines. The copolymer may be selected such that it forms a nanoparticle comprising a core suitable to encapsulate the photosensitive compound. FIG. 1 is a schematic diagram of a polymer nanoparticle with multiple phthalocyanines encapsulated in the core. In some embodiments, the copolymer is selected such that it forms a polymer nanoparticle comprising a hydrophobic core and a hydrophilic outer surface. In certain embodiments, the copolymer and any R group on the phthalocyanines, such as the trihexyl silyloxy group in SiNc, are selected such that the phthalocyanines will be encapsulated in the nanoparticle core forming stable aqueous nanoparticles.

In some embodiments, the copolymer comprises a polyethylene glycol (PEG) moiety. The copolymer may also comprise one or more additional monomers. The additional monomer(s) may be selected to provide an environment suitable to encapsulate the photosensitive compound. Suitable additional monomers include, but are not limited to, polyesters, polyacids and polylactones.

In certain embodiments, the copolymer is polyethylene glycol-block-polycaprolactone (PEG-b-PCL), methoxy polyethylene glycol-block-polycaprolactone (mPEG-b-

PCL), polyethylene glycol-block-polyvalerolactone (PEG-b-PVL), polyethylene glycol-block-polylactic acid (PEG-b-PLA) or polyethylene glycol-block-poly(lactic acid-co-glycolic acid) (PEG-b-PLGA). In certain embodiments, the polymer is mPEG-b-PCL. In particular embodiments, the mPEG-b-PCL comprises an mPEG moiety of from 2,000 Da to 8,000 Da, such as from 3,000 Da to 7,000 Da, or from 4,000 Da to 6,000 Da, and a PCL moiety of from 7,000 Da to 13,000 Da, such as from 8,000 Da to 12,000 Da, or from 9,000 Da to 11,000 Da. In one embodiments, the mPEG-b-PCL polymer comprises an mPEG moiety of 5,000 Da and a PCL moiety of 10,000 Da.

In other embodiments, the PEG-b-PVL comprises a PEG moiety of from 1,000 Da to 7,000 Da, such as from 2,000 Da to 5,000 Da, and a PVL moiety of from 8,000 Da to 25,000 Da or more, such as from 10,000 Da to 20,000 Da.

In some embodiments, polymers selected from PEG-PLA 2,000 Da:1,800 Da, 4,000 Da:2,200 Da, or 5,000 Da:10,000 Da; PLA 10,000 Da; PCL 10,000 Da; PLGA 17,000 Da, 76,000 Da, or 69,000 Da; or PEG-PLC 2,000 Da:5,000 Da failed to produce nanoparticles loaded with photosensitive compound. In certain embodiments, these polymers failed to form nanoparticles with photosensitive compounds according to formula I or formula II.

In certain disclosed embodiments, the polymer was

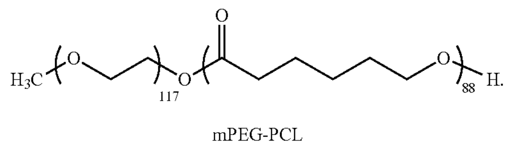

mPEG-PCL

The polymer may be selected to have a molecular weight suitable to form a nanoparticle and encapsulate the phthalocyanines. In some embodiments, the polymer has a molecular weight of from about 10,000 Da to 20,000 Da, such as from 13,000 Da to 17,000 Da. As used herein, the "molecular weight" is a weight averaged molecular weight determined by proton NMR and size exclusion chromatography. In certain embodiments, the copolymer had an average molecular weight that is from 13,500 Da to 16,500 Da, advantageously about 15,000 Da.

C. Targeting Moiety

In some embodiments, the composition comprises a targeting moiety. The targeting moiety is any moiety that can target or direct the composition to a particular site of action, thereby promoting accumulation at that site, and/or reducing systemic distribution. Suitable targeting moieties include, but are not limited to, peptides, proteins, small molecules (for example, folic acid), nucleic acid sequences or antibodies. In some embodiments, the targeting moiety is covalently attached to the polymer nanoparticle. However, in alternative embodiments, the composition does not comprise a targeting moiety.

In some embodiments, the targeting moiety is covalently attached to the polymer nanoparticle. In certain embodiments, the targeting moiety is attached to a PEG moiety on the polymer. There are numerous methods to attach the targeting moiety to the polymer nanoparticle, as a person of ordinary skill in the art will understand. Additional information concerning coupling techniques is provided by Greg T. Hermanson in *Bioconjugate Techniques;* Academic Press, 1996, which is incorporated herein by reference. The percentage of targeting moiety attached to the nanoparticle may be any amount suitable to facilitate targeting the nanoparticle to a desired organ or tumor. In some embodiments, the amount of targeting moiety attached to the nanoparticle is from greater than zero to 50% or more, weight/weight (weight of polymer labeled with targeting moiety/weight of non-labeled polymer), such as from 1% to 50%, or from 5% to 25%. That is, from greater than zero to 50% of the polymer present in the nanoparticle is labeled with the targeting moiety. In particular embodiments, the amount of targeting moiety used was 1%, 5%, 10%, 25% or 50% w/w targeting moiety-polymer/non-labeled polymer.

In some embodiments, the targeting moiety is a peptide that preferentially targets the composition to cancer cells. In some embodiments, the peptide is targeted to a receptor that is overexpressed in cancer cells, is not detectably expressed in non-cancer cells, is mutated in cancer cells, or any combination thereof. In certain embodiments, the peptide is luteinizing-hormone-releasing hormone (LHRH). Exemplary LHRH peptides include, but are not limited to, Gln-His-Trp-Ser-Tyr-DLys(DCys)-Leu-Arg-Pro-NH-Et; Glp-His-Trp-Ser-Tyr-D-Lys-Leu-Arg-Pro-Gly-$NH_2$; and Glp-His-Trp-Ser-His-Asp-Trp-Lys-Pro-Gly-$NH_2$.

Figure 26:
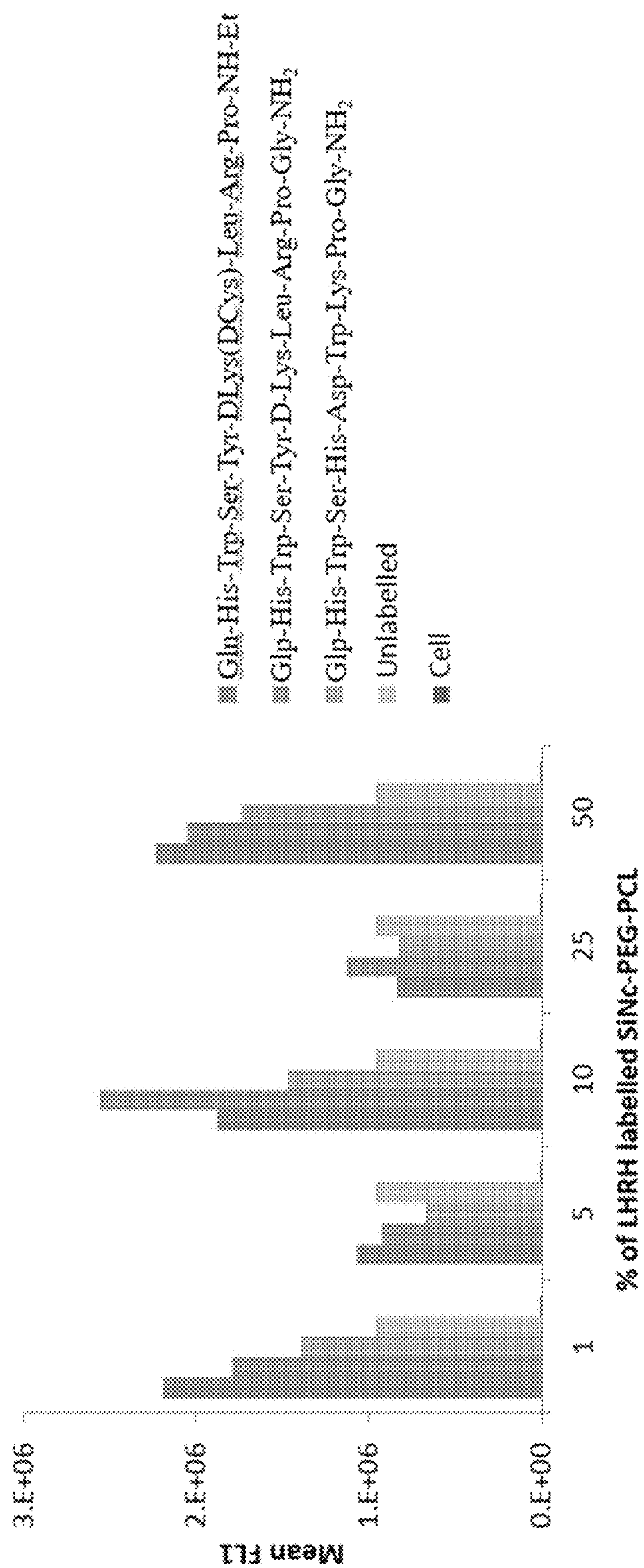
FIG. 26 is a graph of fluorescence versus percentage of LHRH-labelled SiNc-PEG-PCL, illustrating that treatment of ovarian cancer cells with labeled nanoparticles demonstrated higher nanoparticle and SiNc uptake than cells treated with unlabeled nanoparticles. The untreated cell is used as a control.

FIG. 26 provides flow cytometry analysis of ovarian A2780/CDDP cancer cells after treatment for 24 hours with three LHRH-labeled nanoparticles (at different % of corresponding LHRH) and unlabeled nanoparticles. Untreated cells were used as control (navy blue). All SiNc-PEG-PCL particles were conjugated with FITC dye for uptake visualization. Mean fluorescence intensity was used to compare the uptake efficiency in all samples. All nanoparticle modified with LHRH (blue, orange and grey) demonstrated higher cellular uptake as compare to the unlabeled nanoparticles (yellow) at different % of labeled LHRH (1, 5, 10, 25, and 50% w/w LHRH-polymer/non-labeled polymer).

IV. Method of Making the Composition

Figure 2:
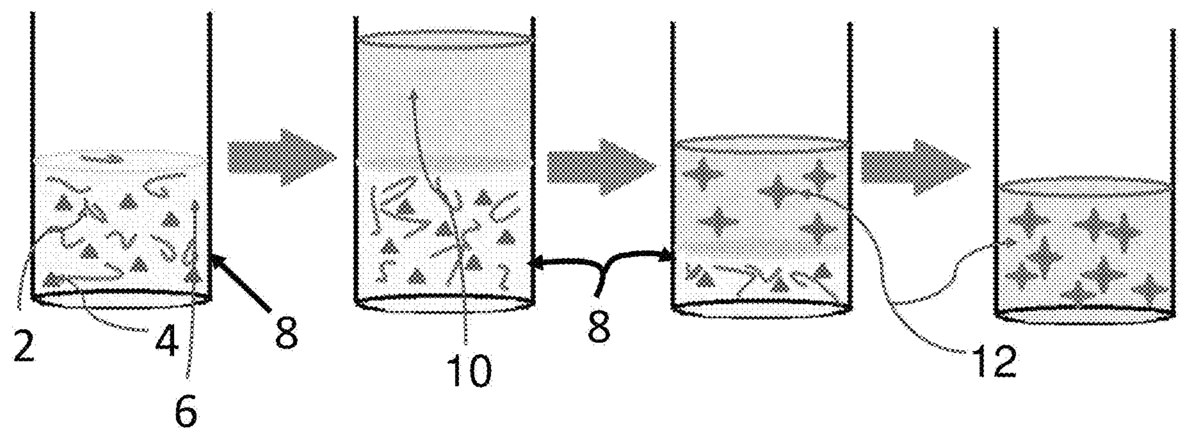
FIG. 2 is a schematic diagram illustrating an exemplary embodiment of the method of making the disclosed compositions.

A general method of forming the composition comprises dissolving the phthalocyanines and polymer is a suitable solvent, adding water and evaporating the solvent. FIG. 2 is a schematic diagram illustrating the general method. With reference to FIG. 2, polymer 2 and phthalocyanines 4 are dissolved in a solvent 6 to form solution 8. The solvent 6 can be any solvent that dissolves both the polymer and the phthalocyanines. Suitable solvents include, but are not limited to, tetrahydrofuran (THF) and dimethylsulfoxide (DMSO). The solvent may be miscible with water, and in some embodiments, the solvent has a boiling point lower than the boiling point of water.

In some embodiments, the amount of polymer and the amount of photosensitive compound are selected to provide a desired amount of loading of the photosensitive compound in the polymer nanoparticle. In some embodiments, the ratio of polymer to photosensitive compound is from greater than 500:1 by weight to less that 10:1 by weight, such as 500:1, 400:1, 350:1, 333:1, 300:1, 250:1, 200:1, 150:1, 100:1, 50:1, 100:3, 25:1, 20:1, 100:6, or 10:1. In certain embodiments, the ratio of polymer to compound was 333:1, 50:1, 100:3, 33:1, 100:6 or 16.67:1.

In some embodiments, water 10 is added to the solution 8, but in other embodiments, the solution 8 is added to the water 10. The addition of the water to the solution may result in the formation of an emulsion. In some embodiments, the amounts of the water 10 and solvent 6 are about equal, but in other embodiments, more or less water 10 is used, compared to the amount of solvent 6. The water 10 and/or solution 8 may be agitated during the addition, such as by shaking or stirring. In some embodiments, the water 10 is added to the solution 8, or vice versa, rapidly, such as in one portion or in a rapid stream.

The solvent 6 is then evaporated. The evaporation can be performed by any suitable technique known to a person of ordinary skill in the art. The solvent may be evaporated rapidly, and in some embodiments, the evaporation is performed under vacuum, such as by a rotary evaporator. In certain embodiments, the evaporation is performed at ambient temperature, i.e. without external heating or cooling, but in other embodiments, the evaporation may be performed with external heating or external cooling. During the evaporation, polymer nanoparticles 12 loaded with the phthalocyanines form in the water 10. The loaded nanoparticles 12 may form as an emulsion or nanosuspension in the water, that is, the polymer nanoparticles are dispersed in the water, such as in a suspension. In some embodiments, the polymer nanoparticles are monodispersed, that is, the polymer nanoparticles have a substantially uniform size in a dispersed phase. In certain embodiments, the nanoparticles do not form a precipitate. The loaded nanoparticles 12 are then collected by any suitable technique, such as centrifugation, filtration or a combination thereof.

In some embodiments, the loaded polymer nanoparticle has a size of from greater than zero to at least 250 nm, such as from 5 nm to 100 nm, from 10 nm to 75 nm or from 25 nm to 50 nm. In certain embodiments, the loaded polymer nanoparticle had a size of from 35 nm to 40 nm as determined by Dynamic Light Scattering (DLS). Cryogenic transmission electron microscopy (cryo-TEM) images revealed a spherical morphology for SiNc-NP with an average size of 19.3±1.5 nm (FIG. 3) and further confirmed preparation of highly monodisperse nanoparticles by using the developed approach In some embodiments, the polymer nanoparticles have an encapsulation efficiency of from 75% to 100%, such as from 80% to 100%, from 90% to 100%, from 95% to 100% or from 97% to 100%. Drug encapsulation efficiency is the percentage of drug weight encapsulated into the nanoparticles compared to the total weight of the drug used for the drug loading procedure. In certain embodiments, the polymer nanoparticles had an encapsulation efficiency of from 98% to 100%.

In some embodiments, the phthalocyanines are loaded in the polymer nanoparticles at a concentration of from greater than zero to 2 mg/mL or greater, such as from 0.01 mg/mL to 2 mg/mL, from 0.01 mg/mL to 1 mg/mL, from 0.02 mg/mL to 0.8 mg/mL, or from 0.03 mg/mL to 0.75 mg/mL. That is, in one mL of polymer solution typically comprising 10 mgs of polymer, there is from greater than zero to 2 mg of phthalocyanines. In certain embodiments, the concentration is from 0.01 mg/mL to less than 0.4 mg/mL, such as from 0.05 mg/mL to 0.3 mg/mL. In certain other embodiments, the concentration is from 0.4 mg/mL to 2 mg/mL or greater, such as from 0.4 mg/mL to 1 mg/mL, from 0.4 mg/mL to 0.75 mg/mL, or from 0.4 mg/mL to 0.6 mg/mL. In certain embodiments, the concentration of the phthalocyanines loaded into the polymer nanoparticles was 0.6 mg/mL and in other embodiments, the concentration was 0.05 mg/mL or 0.3 mg/mL. That is, there were 0.6 mg, 0.05 mg or 0.3 mg of the phthalocyanines per mL of 10 mg/mL nanoparticle solution. In other embodiments, the phthalocyanines are loaded into the nanoparticles at a loading efficiency of from greater than zero to 20%, such as from 0.1% to less than 4%, or from 0.5% to 3%. Typically, such loading efficiencies are suitable for an 'always ON' nanoparticle. In certain other embodiments, the loading efficiency is from 4% to 20% or greater, such as from 4% to 10%, from 4% to 7.5%, or from 4% to 6%. Typically, such loading efficiencies are suitable for an 'OFF-ON' nanoparticle. In certain embodiments, the loading efficiency was 6%, and in other embodiments, the loading efficiency was 0.5% or 3%. Loading efficiency is calculated as amount of phthalocyanines (mg)/amount of polymer (mg)×100%.

In some embodiments, the concentration of phthalocyanines in the polymer nanoparticles is selected such that a solution of the nanoparticles produces a fluorescence emission, such as a high fluorescence emission, when exposed to light at a particular wavelength. In such embodiments, the concentration may be from greater than zero to less than 0.4 mg/mL, such as from 0.01 mg/mL to less than 0.4 mg/mL, or from 0.05 mg/mL to 0.3 mg/mL.

In some embodiments, the concentration of phthalocyanines in the polymer nanoparticles is selected such that phthalocyanine fluorescence is substantially quenched in the solution prior to administration, but a fluorescent signal is produced after administration and accumulation of the drug in a tumor or organ, and exposure of the tumor or organ to light. Such embodiments may be referred to as an 'OFF-ON' system, whereby the fluorescence is OFF when the phthalocyanine is in solution, but ON when, and if, the drug accumulates in a tumor or organ. In such embodiments, the concentration of the phthalocyanines loaded into the polymer nanoparticles may be from 0.4 mg/mL to 2 mg/mL or greater, such as from 0.4 mg/mL to 1 mg/mL, from 0.4 mg/mL to 0.75 mg/mL, or from 0.4 mg/mL to 0.6 mg/mL.

Figure 22:
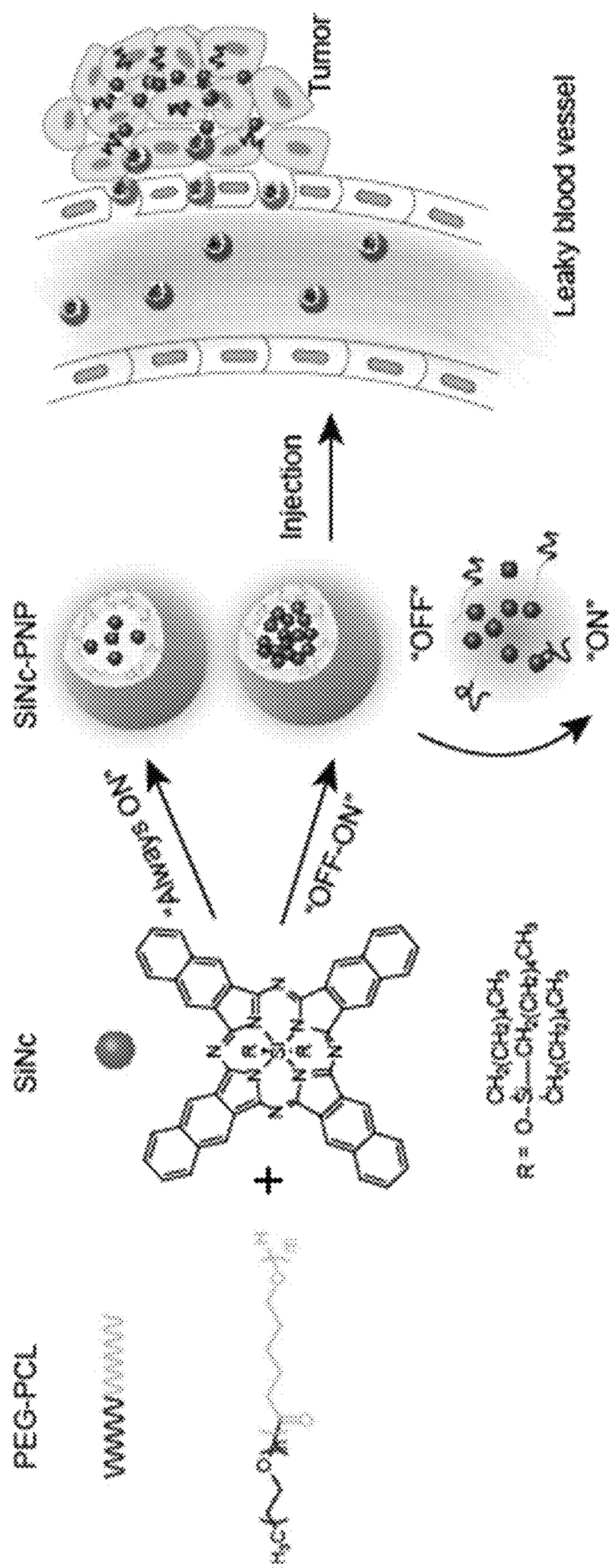
FIG. 22 is a schematic diagram illustrating the similarities and differences between the “always ON” and “OFF-ON” nanoplatforms.

FIG. 22 provides a schematic illustration of the "OFF-ON" and "Always ON" theranostic nanoplatforms. Both platforms comprise a NIR theranostic agent, such as silicon naphthalocyanine (SiNc), and a co-polymer, such as PEG-PCL, as a nanocarrier. The activatable (OFF-ON) SiNc-PNP was tailored to be non-fluorescent ("OFF") and maintain "OFF" till reaching the tumor site. Upon intratumoral accumulation, the OFF/ON SiNc-PNPs disintegrate, releasing the fluorescent compound into the tumor. The photosensitive compound therefore is no longer self-quenching due to concentration, and thus NIR fluorescence is activated. In the always ON platform, the concentration of the photosensitice compound in the nanoparticle is sufficiently low that the photosensitive compound does not self-quench, and thus the NIR fluorescence can be detected at any time post injection.

Figure 23:
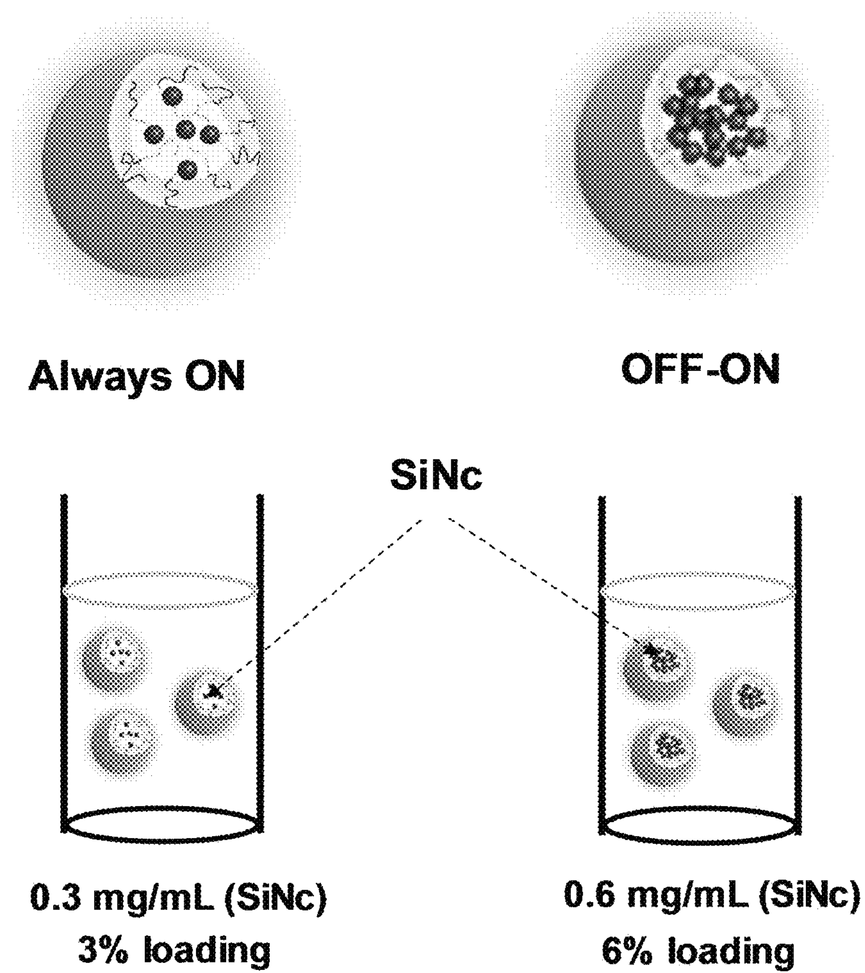
FIG. 23 is a schematic diagram illustrating the different loadings of the photosensitive compound in the nanoparticle for the “always ON” and “OFF-ON” nanoplatforms.

FIG. 23 is a schematic diagram illustrating the different loading in the two theranostic nanoplatforms. Different amount of SiNc were loaded into the PEG-PCL nanoparticles. The "Always ON" (3% SiNc loading at 0.3 mg/mL SiNc) nanoplatform exhibited strong fluorescence signal, and "OFF-ON" (6% SiNc loading at 0.6 mg/mL SiNc) demonstrated fluorescence quenching.

Figure 24:
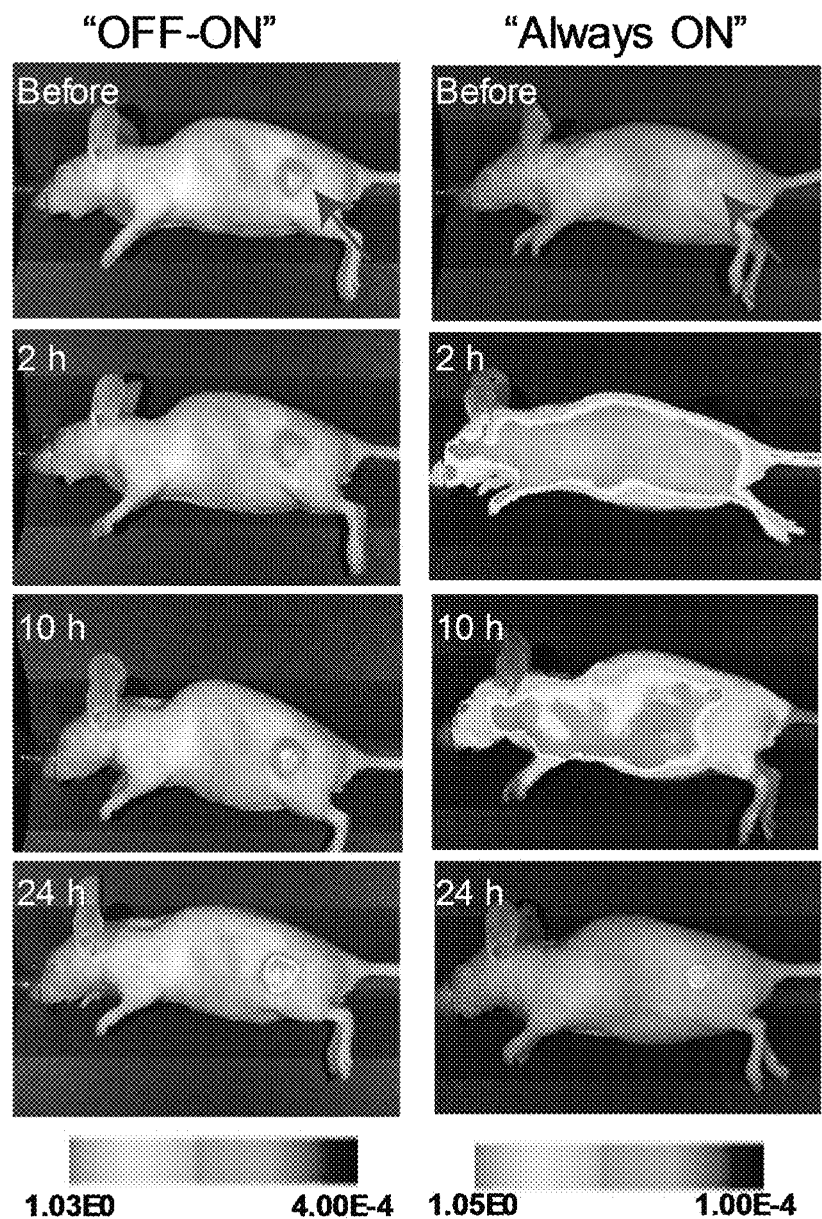
FIG. 24 is a digital image of NIR fluorescence before injection and at 2, 10 and 24 hours post-injection, illustrating the bio-distribution over time of an “always ON” and an “OFF-ON” nanoplatform disclosed herein, and that after 24 hours, both platforms accurately identify the subcutaneous cancer tumor.
Figure 25:
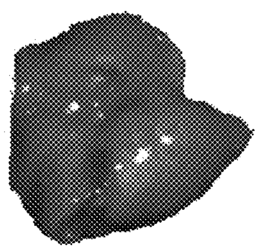
FIG. 25 is a digital image of NIR fluorescence images of various organs and tumors that were acquired from mice at 24 hours post-injection.
Figure 25:
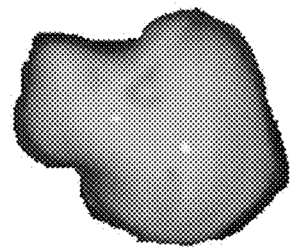
Figure 25:
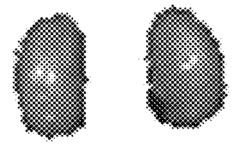
Figure 25:
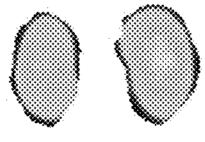
Figure 25:
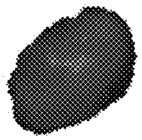
Figure 25:
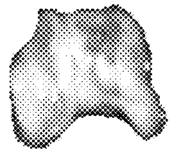
Figure 25:
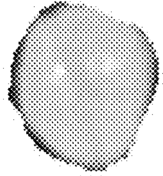
Figure 25:
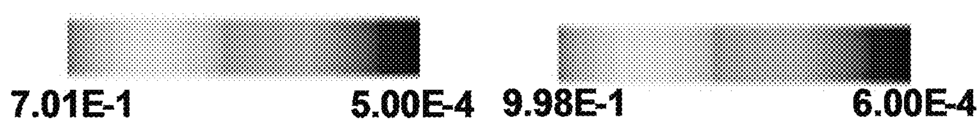

FIG. 24 demonstrates how the always ON and OFF-ON nanoplatforms differ in their respective approaches but provide similar results. With respect to FIG. 24, the left hand images show the progression of the OFF-ON platform over 24 hours post-i.v. injection, whereas the right hand images illustrate the always ON progression. As FIG. 24 clearly demonstrates, the OFF-ON nanoplatform does not provide a fluorescent signal immediately. Rather, after being administered systemically, the signal selectively builds up over time in the tumor, as the platform accumulated there and releases the photosensitive compound. In contrast, the always ON nanoplatform provides a large and non-specific signal 2 hours after injection. This signal decreases over 24 hours until just the signal due to the compound in the tumor remains. And FIG. 25 provides fluorescent images of various organs and tumors acquired at 24 hours post-injection. As can be seen in FIG. 25, after 24 hours the OFF-ON nanoplatform only provided a strong fluorescent signal in the tumor, and with the always ON nanoplatform, in addition to a strong fluorescent signal in the tumor, less intense fluorescent signals could be detected in a couple of organs.

V. Method of Using the Composition

PDT is a non-invasive clinical modality that involves the administration of a non-toxic photoactive drug (photosensitizer), which, after irradiation by a non-thermal light, causes the formation of cytotoxic ROS that can damage cancer tissue. In addition to the therapeutic effect, the light induced excitation of photosensitizers can also result in fluorescence emission, allowing photoactive drugs to act as both therapeutic and imaging agents. Unlike for PDT, PTT agents absorb the light and convert it into heat, which is then transferred to the intracellular environment, generating localized hyperthermia. As PDT and PTT act against cells via different mechanisms, their combination into the single therapeutic modality provides a highly efficient approach to treat cancer tumors, particularly solid tumors. Exemplary types of cancer that the disclosed compositions are useful for treating include, but are not limited to, ovarian cancer, breast cancer, prostate cancer, pancreatic cancer, head and neck cancer, liver cancer and skin melanomas. The dual functionality of the composition, acting through unconnected mechanisms, significantly reduces the likelihood of the cells developing resistance to the therapy. Additionally, to avoid multiple administrations of different therapeutic agents and improve patient compliance, it is highly desirable to have a single nanomedicinal platform that possesses both the PDT and PTT therapeutic functions.

One of the major challenges in the clinical application of both PDT and PTT is that the visible light used to activate the appropriate therapeutic agents can only penetrate through several millimeters of tissue. Therefore, it is advantageous that PDT and PTT agents exhibit strong absorbance in the NIR region, which is a transparency window for biological tissues, and that they can efficiently transfer the absorbed NIR optical energy into ROS and heat, respectively. Moreover, fluorescence imaging in the NIR optical window holds much promise due to minimal tissue autofluorescence and light scattering. Thus, the accumulation of PDT and PTT agents in metastatic tumors can be followed by monitoring the fluorescence emission of the photosensitizer after systemic administration. Phototherapy can then be precisely applied to a detected region by selectively illuminating the cancer tissue with light of an appropriate wavelength, while leaving health organs untouched.

For example, the high mortality rate among patients with metastatic ovarian cancer is attributed, in part, to the fact that only surgical removal of most abdominal metastases may reduce cancer recurrence and enhance the effect of post-operative chemotherapy. Unfortunately, even with the best microsurgical techniques, resection leaves behind residual microscopic tumors that can eventually lead to cancer relapse. Furthermore, the efficacy of post-operative chemotherapy is significantly limited by the resistance of ovarian cancer cells to chemotherapeutic agents and the severe systemic side effects that non-targeted chemotherapeutic agents have on healthy organs.

Embodiments of the composition disclosed herein provide a theranostic nanomedicinal platform that enables imaging and maximal treatment of un-resected and/or chemo-resistant ovarian cancer cells using an intraoperative multimodal phototherapy. A low level exposure to the correct wavelength of light will illuminated the tumor, thereby guiding the surgeon. After surgery, because the composition is targeted to the cancer cells, optionally through the targeting moiety, and/or because the light is targeted specifically to the desired location, exposure to a stronger light source selectively kills any remaining cancer cells, while leaving healthy cells alone. The synergistic effect of the combined noninvasive photodynamic (PDT) and photothermal (PTT) therapy is expected to improve the therapeutic efficiency, overcome multidrug resistance and decrease the dosage-limiting toxicity of current chemotherapy drugs. However, the disclosed composition can also be used in combination with chemotherapeutic agents and/or radiation therapy for the treatment of certain diseases, including cancer.

The light may be produced by a laser. In certain embodiments, the laser power was from less than 0.2 W/cm$^2$ to greater than 1.5 W/cm$^2$, such as from 0.3 W/cm$^2$ to 1.3 W/cm$^2$. In particular embodiments, the laser power is selected to achieve a particular effect. For example, a laser power of about 0.3 W/cm$^2$ may result in a PDT effect, and laser powers of from about 0.8 W/cm$^2$ to about 1.3 W/cm$^2$, such as 0.8 W/cm$^2$, 1 W/cm$^2$, or 1.3 W/cm$^2$ may result in a PTT effect.

VI. Pharmaceutical Compositions and Administration

A. Additional Therapeutic Agents

Pharmaceutical compositions are disclosed that include one or more embodiments provided herein and typically at least one additional substance, such as an excipient, a known therapeutic other than those of the present disclosure, or combinations thereof. In some embodiments, the disclosed compositions can be used in combination with other agents known to have beneficial, additive or synergistic activity with the disclosed compositions. For example, disclosed compositions can be administered alone or in combination with one or more additional agents, for treating liquid, solid and/or metastatic tumors. Exemplary chemotherapeutic agents include agents that interfere with DNA replication, mitosis and chromosomal segregation, agents that disrupt the synthesis and fidelity of polynucleotide precursors, alkylating agents, antimetabolites, cytotoxic antibiotics, vinca alkaloids, tyrosine kinase inhibitors, metalloproteinase and COX-2 inhibitors, cyclophosphamide, cisplatin, docetaxel, paclitaxel, erlotinib, irinotecan, gemcitabine and cisplatin. Other particular chemotherapeutic agents that can be used in combination with the disclosed compounds include alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide); microtubule binding agents (such as paclitaxel, docetaxel, vinblastine, vindesine, vinorelbine (navelbine) vincristine, the epothilones, colchicine, dolastatin 15, nocodazole, podophyllotoxin, rhizoxin, and derivatives and analogs thereof), DNA intercalators or cross-linkers (such as cisplatin, carboplatin, oxaliplatin, mitomycins, such as mitomycin C, bleomycin, chlorambucil, cyclophosphamide, and derivatives and analogs thereof), DNA synthesis inhibitors (such as methotrexate, 5-fluoro-5'-deoxyuridine, 5-fluorouracil and analogs thereof); anthracycline family members (for example, daunorubicin, doxorubicin, epirubicin, idarubicin, mitoxantrone, and valrubicin); antimetabolites, such as cytotoxic/antitumor antibiotics, bleomycin, rifampicin, hydroxyurea, and mitomycin; topoisomerase inhibitors, such as topotecan and irinotecan; photosensitizers, such as aminolevulinic acid, methyl aminolevulinate, porfimer sodium, and verteporfin, enzymes, enzyme inhibitors (such as camptothecin, etoposide, formestane, trichostatin and derivatives and analogs thereof), kinase inhibitors (such as imatinib, gefitinib, and erolitinib), gene regulators (such as raloxifene, 5-azacytidine, 5-aza-2'-deoxycytidine, tamoxifen, 4-hydroxytamoxifen, mifepristone and derivatives and analogs thereof); and other agents, such as alitretinoin, altretamine, amsacrine, anagrelide, arsenic trioxide, asparaginase, axitinib, bexarotene, bevacizumab, bortezomib, celecoxib, denileukin diftitox, estramustine, hydroxycarbamide, lapatinib, pazopanib, pentostatin, masoprocol, mitotane, pegaspargase, tamoxifen, sorafenib, sunitinib, vemurafinib, vandetanib, and tretinoin. In one instance, the disclosed compounds are used in combination with a biologic for treating cancer (e.g., an antibody, such as a humanized antibody, which can be polyclonal, monoclonal, or chimeric, for example alemtuzumab, bevacizumab, cetuximab, gemtuzumab, rituximab, panitumumab, pertuzumab, or trastuzumab).

B. Excipients and Dosage Forms

The present disclosure provides pharmaceutical compositions that include a therapeutically effective amount of one or more disclosed compositions (such as 1, 2, 3, 4 or 5 disclosed compositions) in admixture with at least one pharmaceutically acceptable material, such as an excipient. Disclosed pharmaceutical compositions include a detectable amount of the photosensitive compound, such as greater than 0% to less than 100%, such as from 5% to 99%, or from about 50% to about 99%, or from 25% to about 99% by weight of the composition of the present disclosure.

Disclosed compositions can be administered in any suitable dosage form, such as tablets, pills, capsules, powders, granules, sterile solutions or suspensions, metered aerosol or liquid sprays, drops, ampoules, auto-injector devices or suppositories. The compositions are intended for any suitable administration route, including oral, topical, parenteral, intranasal, sublingual, rectal, transdermal, inhalation, insufflation or direct injection into a tumor. The compositions may be formulated by methods known by those of ordinary skill in the art, such as described in Remington's Pharmaceutical Sciences (15th ed., Mack Publishing Company, Easton, Pa., 1980).

The compositions can be administered for therapeutic treatments. In therapeutic applications, compositions are administered to a subject suffering from a disease (e.g., a cancer or tumor) in a "therapeutically effective amount." The subject may be a mammal, such as a human, canine, feline, rodent, monkey or ape. Amounts effective for this use can depend upon the severity of the disease and the general state of the subject's health. Single or multiple administrations of the compositions can be administered depending on the dosage and frequency as required and tolerated by the subject. Also, the composition, shape, and type of dosage forms may vary depending on their use. Similarly, a parenteral dosage form may contain smaller amounts of the active ingredient than an oral dosage form.

Oral dosage forms include, but are not limited to, tablets (including, without limitation, scored or coated tablets), pills, granules, lozenges, caplets, capsules, chewable tablets, powder packets, cachets, troches, wafers, aerosol sprays, mucosal patches, or liquids, such as syrups, elixirs, solutions, or suspensions in an aqueous liquid, for example water or saline, a non-aqueous liquid, an oil-in-water emulsion, or a water-in-oil emulsion. Typical oral dosage forms may be prepared by combining the pharmaceutically acceptable composition, potentially in a liquid, solid, granule or gelatin form and/or in a salt form, in admixture with at least one excipient including, but are not limited to, surface stabilizers, dispersion aids, binders, filling agents, lubricating agents, glidants, suspending agents, sweeteners, flavoring agents, preservatives, buffers, wetting agents, disintegrants, effervescent agents, humectants, controlled release agents, absorption accelerators, absorbents, plasticizers, lactose, sucrose, mannitol, sorbitol, calcium phosphates, corn starch, potato starch, cellulose, hydroxy propyl methyl cellulose, microcrystalline cellulose, gelatin, acacia, sodium alginate, alginic acid, tragacanth, guar gum, gelatin, colloidal silicon dioxide, talc, magnesium stearate, stearic acid, colorants, diluents, talc, calcium carbonate, kaslin, maltodextrin, polymethacrylates, moistening agents, preservatives, dyes, and any combination thereof.

Disintegrants facilitate producing tablets that disintegrate when exposed to an aqueous environment. The amount of disintegrant used varies based upon the type of formulation and mode of administration, and is readily determined by a person of ordinary skill in the art. Typical pharmaceutical compositions comprise from about 0.5 to about 15 weight percent of disintegrant, such as from about 1 to about 5 weight percent of disintegrant. Disintegrants include, but are not limited to, agar-agar, alginic acid, guar gum, calcium carbonate, microcrystalline cellulose, croscarmellose sodium, carboxymethylcellulose calcium, methylcellulose, crospovidone, polacrilin potassium, sodium starch glycolate, potato or tapioca starch, other starches, pre-gelatinized starch, clays, other algins, other celluloses, gums, and mixtures thereof.

Exemplary lubricants include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), sodium benzoate, sodium stearylfumarate, zinc stearate, ethyl oleate, ethyl laureate, agar, syloid silica gel, synthetic silica, and mixtures thereof. Lubricants typically are used in an amount of less than about 1 weight percent of the pharmaceutical compositions.

Pharmaceutical compositions can also include large, slowly metabolized macromolecules such as proteins, polysaccharides, such as chitosan, polylactic acids, polyglycolic acids and copolymers (such as agarose, cellulose, and the like), polymeric amino acids, amino acid copolymers, and lipid aggregates (such as oil droplets or liposomes). Additionally, these carriers can function as immunostimulating agents (i.e., adjuvants).

The compositions provided herein, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories. Exemplary suppositories include a suppository base, such as natural or synthetic triglycerides or paraffin hydrocarbons. Gelatin rectal capsules include a combination of the compound of choice with a base, including, for example, liquid triglycerides, polyethylene glycols, and paraffin hydrocarbons.

Topical dosage forms include, but are not limited to, creams, lotions, ointments, gels, shampoos, sprays, aerosols, solutions, emulsions, and other forms know to a person of ordinary skill in the art. Suitable formulations include, without limitation, solutions, suspensions, emulsions, creams, ointments, powders, liniments, and salves.

Transdermal and mucosal dosage forms can include, but are not limited to, ophthalmic solutions, patches, sprays, aerosols, creams, lotions, suppositories, ointments, gels, solutions, emulsions, or suspensions. Dosage forms suitable for treating mucosal tissues within the oral cavity can be formulated as mouthwashes, as oral gels, or as buccal patches.

The disclosed compositions can be formulated for parenteral administration, such as, for example, by intraarticular (in the joints), intravenous, intraarterial, intramuscular, intratumoral, intradermal, intraperitoneal, direct injection into a tumor, topical and subcutaneous routes. Parenteral dosage forms include, but are not limited to, solutions ready for injection, dry products ready to be dissolved or suspended in a pharmaceutically acceptable vehicle for injection, suspensions ready for injection, and emulsions. Suitable materials for such administration include sterile water; saline solution; glucose solution; aqueous vehicles, such as sodium chloride injection, Ringer's injection, dextrose injection, dextrose, lactated Ringer's injection; ethyl alcohol, polyethylene glycol, and propylene glycol; non-aqueous vehicles such as, but not limited to, corn oil, cottonseed oil, peanut oil, sesame oil, ethyl oleate, isopropyl myristate, and benzyl benzoate; aqueous and non-aqueous, isotonic sterile injection solutions, which can contain antioxidants, buffers, bacteriostats, and solutes that render the formulation isotonic with the blood of the intended recipient; and aqueous and non-aqueous sterile suspensions that can include suspending agents, solubilizers, thickening agents, stabilizers, and preservatives. In the practice of this disclosure, compositions can be administered, for example, by intravenous infusion, orally, topically, intraperitoneally, intravesically, intratumorally, subcutaneously, or intrathecally. In an independent embodiment, parenteral administration, oral administration, intratumoral administration and/or intravenous administration are the methods of administration. The formulations of compounds can be presented in unit-dose or multi-dose sealed containers, such as ampules and vials.

The pharmaceutical preparation can be in unit dosage form. In such form the preparation is subdivided into unit doses containing appropriate quantities of the active component. The unit dosage form can be a packaged preparation, the package containing discrete quantities of preparation, such as packaged tablets, capsules, solutions, suspensions, emulsions, and powders in vials or ampoules. Also, the unit dosage form can be a capsule, tablet, cachet, or lozenge itself, or it can be the appropriate number of any of these in packaged form.

The combined administrations contemplate co-administration, using separate formulations or a single pharmaceutical formulation, and consecutive administration in either order, wherein, in some embodiments, there is a time period while both (or all) active agents simultaneously exert their biological activities.

The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly or monthly etc.) doses over a period of a few days to months, or even years. For example, a therapeutically effective amount of one or more compounds disclosed herein can be administered in a single dose, twice daily, weekly, or in several doses, for example daily such as two, three or four times daily, or during a course of treatment. The disclosed compositions may be administered substantially continuously too, such as by using a transdermal delivery system. In a particular non-limiting example, treatment involves once daily dose or twice daily dose.

The pharmaceutical compositions that include one or more compounds disclosed herein can be formulated in unit dosage form, suitable for individual administration of precise dosages. In one non-limiting example, a unit dosage contains from about 0.1 mg to about 50 g of one or more of the compositions disclosed herein, such as about 1 mg to about 10 g, about 10 mg to about 10 g, about 100 mg to about 7 g, about 200 mg to about 10 g, or about 200 mg to about 5 g. In other examples, a therapeutically effective amount of one or more compositions disclosed herein comprises the photosensitive compound in an amount of from about 0.01 mg/kg to about 500 mg/kg, for example, about 0.5 mg/kg to about 500 mg/kg, about 1 mg/kg to about 100 mg/kg, or about 1 mg/kg to about 50 mg/kg. In other examples, a therapeutically effective amount of one or more compositions disclosed herein comprises the photosensitive compound in an amount of from about 0.01 mg/kg to about 20 mg/kg, such as about 0.1 mg/kg to about 5 mg/kg, or from about 0.5 mg/kg to about 3 mg/kg.

VII. Examples

Example 1

Preparation of SiNc-PEG-PCL Nanoparticles Formulation

Silicon 2,3-naphthalocyanine bis(trihexylsilyloxide) (SiNc, Sigma-Aldrich, St. Louis, Mo.) was loaded into nanoparticles to increase its water solubility and for passive tumor targeting. The building block for the nanoparticles was Methoxy Poly(ethylene glycol)-b-Polycaprolactone (mPEG-PCL) with the molecular weight of 15000 Da.

20 mg of methoxyPEG$_{5000}$-PCL$_{10000}$ (MW 15000) and (0.12-0.6 mg SiNc were dissolved in 2 mL of THF. The SiNc-polymer solution was stirred constantly and 2 mL of DI $H_2O$ was added in a 1-step process to produce the emulsion. The THF was removed under vacuum using a rotoevaporator and the final volume was adjusted to 2 mL using DI $H_2O$. The resultant nanosuspension was centrifuged at 10,000 rpm for 5 minutes and the supernatant was collected and filtered using a 13 mm 0.2 μM nylon filter. Exemplary SiNc-NP loadings include, but are not limited to, 0.06 mg/mL, from 0.12 mg SiNc and 20 mg polymer; 0.3 mg/mL, from 0.6 mg SiNC and 20 mg polymer; and 0.6 mg/mL, from 1.2 mg SiNc and 20 mg polymer. For in vivo studies, a formulation was prepared in saline.

Example 2

Size and Zeta Potential Measurements

Figure 3:
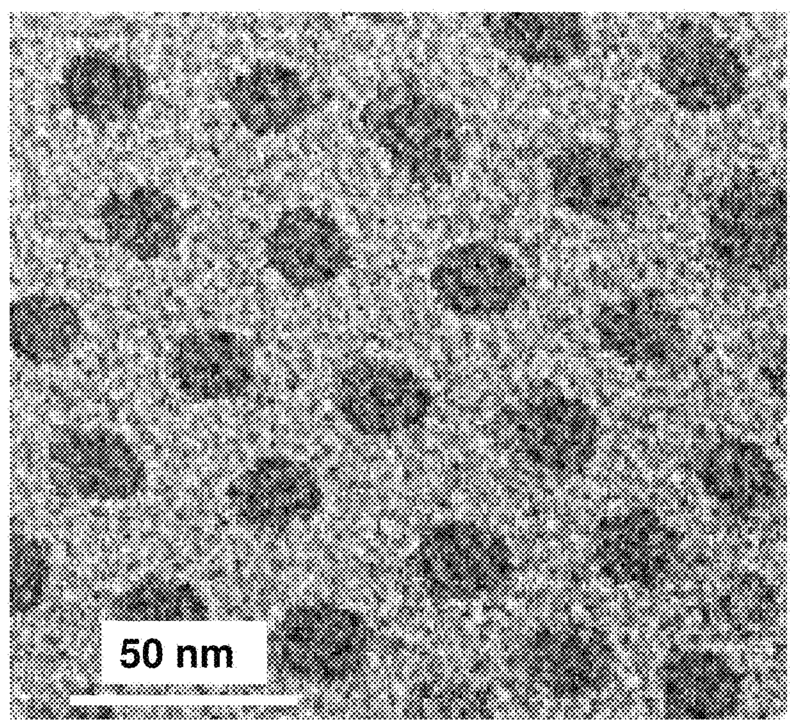
FIG. 3 is an exemplary cryogenic transmission electron microscopy (cryo-TEM) image of silicon 2,3-naphthalocyanine bis(trihexylsilyloxide)-loaded nanoparticles (SiNc-NP).

The hydrodynamic size and zeta potential of the prepared complexes were measured by Malvern ZetaSizer NanoSeries (Malvern Instruments, UK) according to manufacturer's instructions. Samples were diluted with 50 mM PBS buffer (pH 7.4) to yield a final SiNc concentration of about 1.0 μg/mL. The intensity of the He—Ne laser (633 nm) was measured at an angle of 173°. All measurements were performed at 25° C. after pre-equilibration for 2 minutes and each parameter was measured in triplicate. The morphology of the polymeric nanoparticles was observed using cryogenic transmission electron microscopy (cryo-TEM). The 3 μl of nanoparticle suspensions (0.3 mg/ml) were pipetted onto glow-discharged (30 sec, 30 mAmp) copper Quantifoil holey carbon support grids (Ted Pella 658-300-CU) and vitrified on liquid ethane using a Mark IV Vitrobot (FEI, Hillsboro, Oreg.). The conditions utilized were 100% humidity, blot force 0 and blotting times between 2-4 seconds. Low-dose conditions were used to acquire images on a FEI Krios-Titan equipped with a Falcon II direct electron detector (FEI, Hillsboro, Oreg.). Cryo-TEM images were collected with a defocus range of 2-4 μm (FIG. 3).

Example 3

Absorption and Fluorescence Measurements

Absorption and fluorescence spectra of SiNc-NP and SiNc-NP in saline or THF were measured using a UV-1800 spectrophotometer (Shimadzu, Carlsbad, Calif.) and Cary Eclipse R3896 fluorescence spectrophotometer (Varian Inc., Mulgrave Victoria, Australia), respectively.

Example 4

Temperature Evaluation Induced by Laser Irradiation

A continuous wave (CW) 785 nm laser diode (Intense, North Brunswick, N.J., 1.3 W/cm$^2$) operated with the laser diode driver (ThorLabs, Newton, N.J.) was employed. To evaluate the laser induced temperature increase, 300 μL of SiNc-NP aqueous solutions (300 μg/ml) were added into the clear 0.5 mL vials, respectively. Then each vial was irradiated with the laser diode for 20 minutes, while the temperature was monitored with thermocouple thermometer (VWR Int.) at designated time intervals. As a control, 300 μL of dionized water was irradiated at the same laser settings for temperature recording.

Example 5

Singlet Oxygen $^1O_2$ Measurements $^1O_2$ production was evaluated by using Singlet Oxygen Sensor Green (SOSG) assay (Life Technologies, Grand Island, N.Y.). SOSG in the presence of singlet oxygen emits a green fluorescence (excitation/emission max about 504/525 nm). To the parallel wells of the 96 well opaque plate (Corning), 40 μl of the 25 μM stock solution of SOSG in methanol, 50 μL of $H_2O$, and 10 μL of SiNc-NP (SiNc about 100 μg/ml) in MilliQ water were added to give working concentrations of 10 μM SOSG and 10 μg/ml SiNc in a final volume of 100 μL per well. Next, some wells were irradiated with light (785 nm, 0.3 W/cm$^2$, 5 minutes) while the dark control was kept covered. Immediately, the samples were analyzed on Cary Eclipse R3896 fluorescence spectrophotometer (Varian Inc., Mulgrave Victoria, Australia) using an excitation wavelength of 504 nm and emission wavelength of 525 nm. All experiments were performed in triplicate.

Example 6

Photostability

To investigate photostability, absorption spectra of SiNc-NP aqueous solutions were recorded prior to and after 30 minutes irradiation with the laser diode (785 nm, 1.3 W/cm$^2$). Furthermore, light and fluorescence images of the studied solutions before and after irradiation were acquired with Li-COR Pearl Animal Imaging System. The temperature of the studied solutions was monitored with thermocouple thermometer (VWR Int.) at designated time intervals.

Example 7

Characterization

Figure 4:
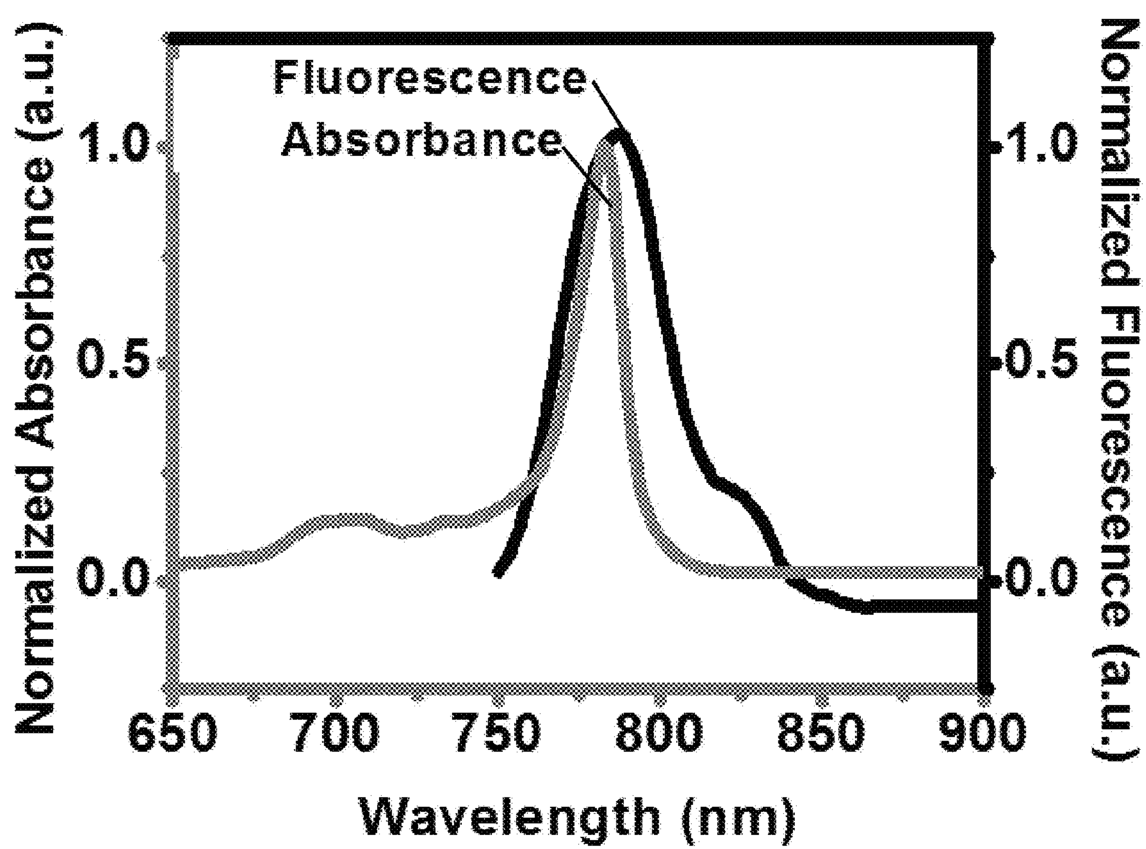
FIG. 4 is a plot of absorbance and fluorescence versus wavelength, illustrating the absorbance and fluorescence characteristics of an exemplary SiNc-containing nanoparticle.

The SiNc-loaded nanoparticles (SiNc-NP) exhibited a strong NIR absorption (about 785 nm) and fluorescence emission (about 790 nm) in water (FIG. 4) upon excitation with NIR light. The detected absorbance and fluorescence fits within the NIR optical window (700-900 nm) required for an efficient intraoperative fluorescence imaging.

Figure 5:
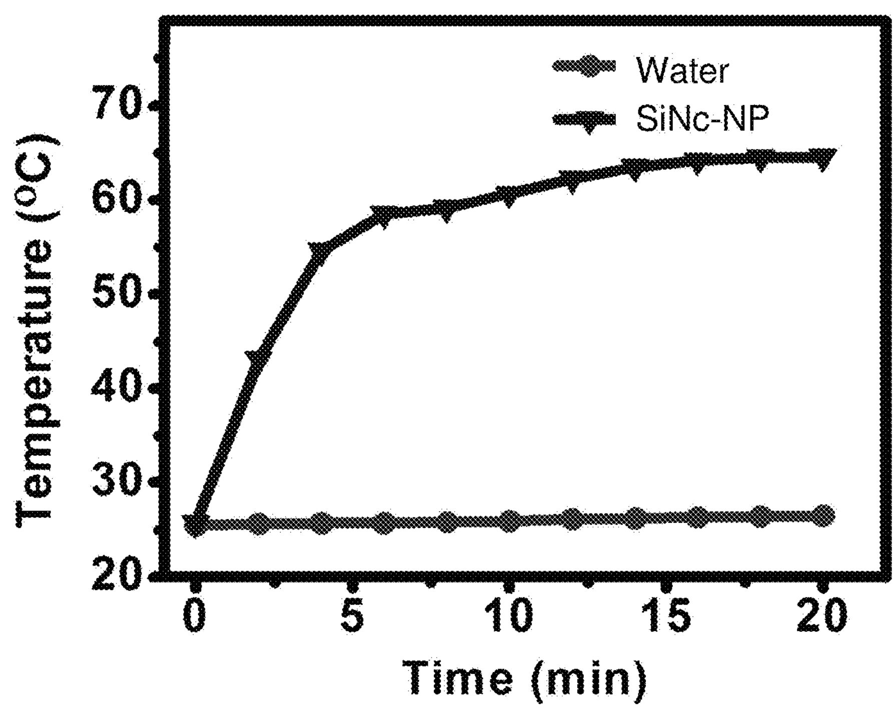
FIG. 5 is a plot of temperature versus time, illustrating the temperature profiles of SiNc-NP (300 μg/mL) exposed to a laser diode at 785 nm and 1.3 W/cm$^2$.
Figure 6:
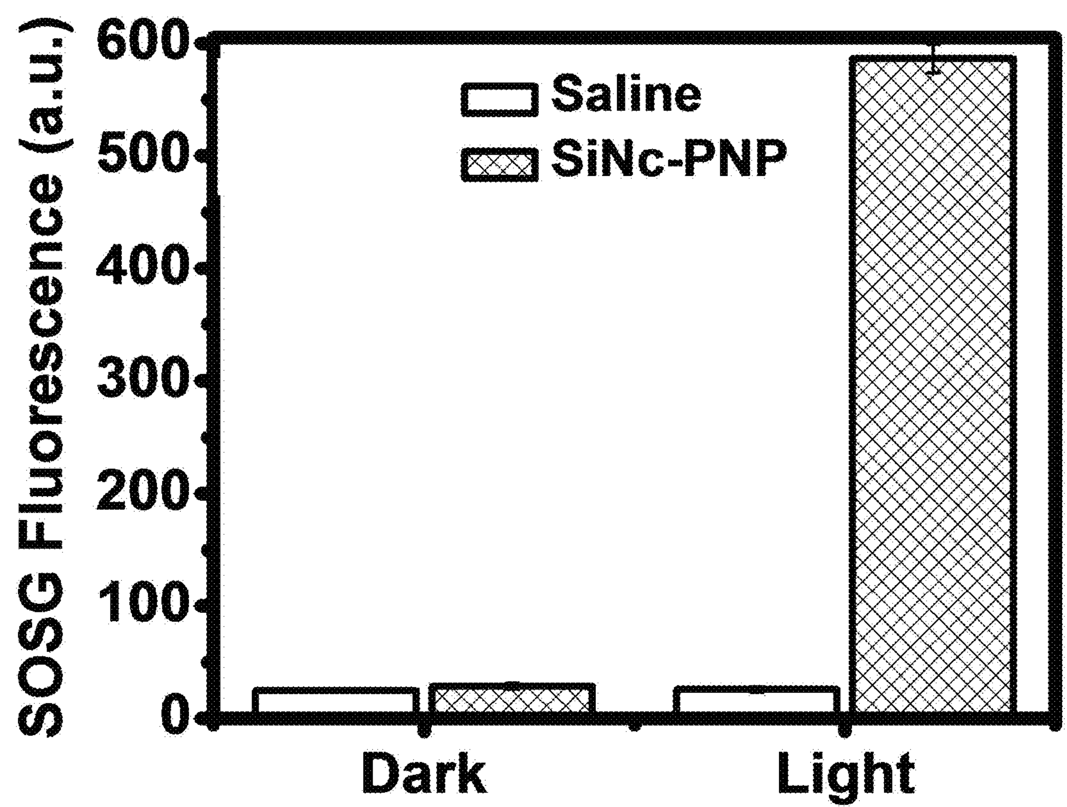
FIG. 6 is a plot of Singlet Oxygen Sensor Green (SOSG) fluorescence in different lighting conditions, illustrating the relative singlet oxygen level in SiNc-NP and a saline control when irradiated for 10 minutes with a 785 nm laser diode.

Furthermore, in the aqueous environment, SiNc-NP exhibited rapid heating to 52° C. upon exposure to NIR light (FIG. 5, triangles), demonstrating that it could be employed as an efficient PTT agent. Concurrently, the SiNc-NP nanosuspension irradiated with the NIR laser light, showed a 600-fold elevation in singlet oxygen level, compared to the controls (FIG. 6), which indicated their potential as PDT agent.

Figure 7:
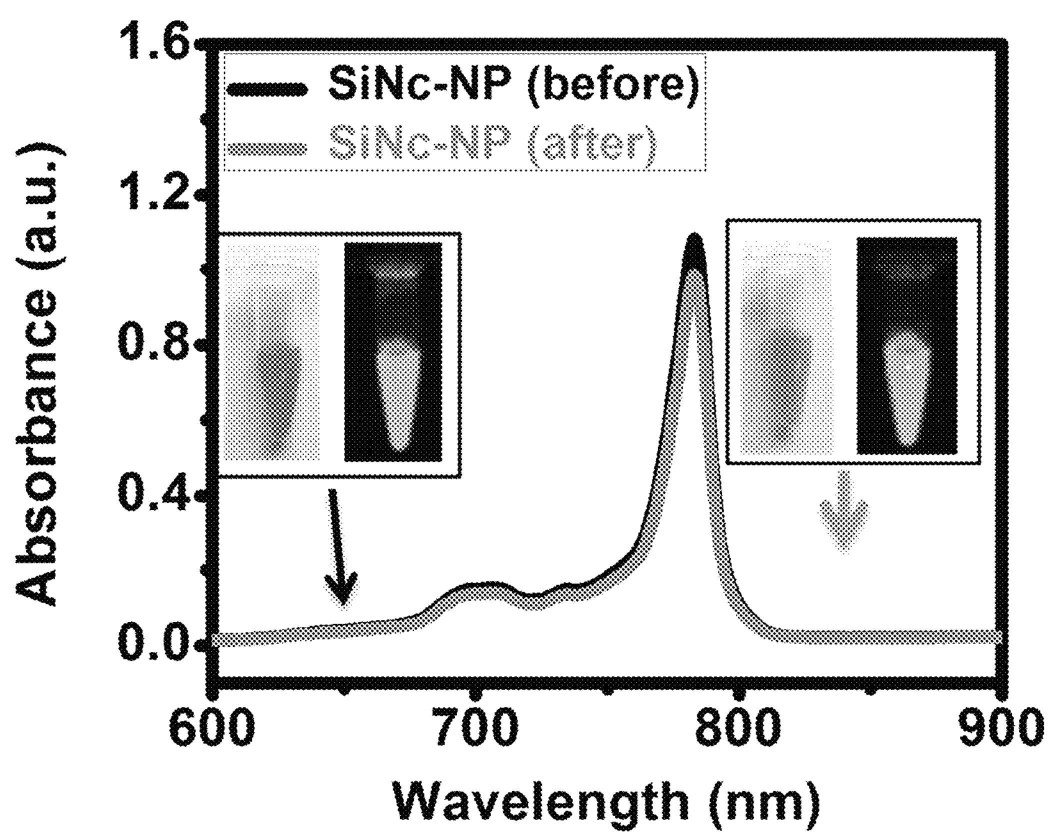
FIG. 7 is a plot of absorbance versus wavelength, illustrating the absorption spectra of SiNc-NP before and after irradiation with the 785 nm laser diode at 1.3 W/cm$^2$ for 30 minutes.

Since during surgery, excitation light will be continually illuminating the surgical field of view, photostability of NIR photoactive agents is an extremely important parameter. If the fluorophores are unstable, it is possible that photobleaching could be misinterpreted as a lack of fluorescence contrast, which would give false negative results to the surgeon. FIG. 7 shows that the nanoparticles encapsulated SiNc exhibits extremely high photostability under fluence rate 26 times higher than the photobleaching threshold for the conventional fluorophores. According to the data, the NIR irradiation of the water solution of SiNc-NP for 30 minutes did not cause a noticeable decrease in absorption or fluorescence intensity of SiNc (FIG. 7), implying photostability. As shown in the FIG. 7 insets, SiNc nanoplatform retained both the green color and fluorescence of naphthalocyanine after 30 minutes of laser irradiation. In addition, SiNc-NP were stable at room temperature for a period of at least two months.

Example 8

In Vivo Study

Tumor Transplantation:

Tumor animal models of human ovarian carcinoma xenografts were established as follows:

Subcutaneous Tumor Model:

Human ovarian carcinoma A2780/AD resistant cells (5×10$^6$) suspended in RPMI 1640 cell culture media were subcutaneously injected into flank of 6-week-old female athymic nu/nu mice purchased from the National Cancer Institute (NCI). The tumor size was measured with a digital caliper (VWR Int.), and the tumor volume was calculated as width$^2$×length×0.5 for 25 days.

Orthotopic Tumor Model:

Human ovarian cancer cells ES2 transfected with firefly luciferase (ES2/Luc) were cultured in RPMI medium with 2 mM glutamine and 10% fetal bovine serum. Cells were then harvested and dispensed in fresh media at a concentration of $3\times10^7$ cells/mL. 200 μL of the cell solution containing about 6 million cells was injected into 6-week-old female athymic nu/nu mice intraperitoneally. For visualization of the orthotopic tumors, D-luciferin, the substrate for luciferase's bioluminescence reaction, was injected into mice intraperitoneally to generate bioluminescence before imaging.

Imaging and Phototherapy:

On post-implantation day 7, when the tumors reached a size of about 40 $mm^3$, the mice were imaged before the SiNc-NP injection using Li-COR Pearl Animal Imaging System with 800 nm channel. The mice were randomly distributed to one of three groups (five mice per group): (1) control, (2) NIR laser, (3) SiNc-NP (dark control), and (4) SiNc-NP+NIR laser (combinatorial treatment). Next, the corresponding tumors underwent i.v. injection of SiNc-NP (300 μg/mL, 100 μL). For accumulation and organ SiNc distribution study, fluorescent images of the whole mice and each organ were obtained at different time points following i.v. injection, and the 24 hour time point demonstrated the highest accumulation of SiNc in the tumor. Thus, after 24 hours, the mice in the particular experimental groups underwent one-time phototherapy (continuous wave laser, 785 nm, 1.3 W/$cm^2$, 10 minutes) under isoflurane anesthesia. After treatment, the mice were monitored daily. Fluorescence imaging, body weight and tumor size were recorded for all mice during 25 days following treatment. In case where the tumors disappeared, the tumor volumes were recorded as "zero". Mice were euthanized at the defined end point when tumor diameter reached 13 mm.

Intratumoral Temperature Monitoring:

During the NIR irradiation, the temperature changes in tumor were measured in 10 second intervals by placing a fiber optic temperature probe (Neoptix Inc., QC, Canada) into a tumor through a thin (18-gauge) needle. The fiber optic probe was protected inside of needle shaft from light exposure to avoid temperature misreading.

Example 9

In Vivo Evaluation

Figures 8A, 8B:
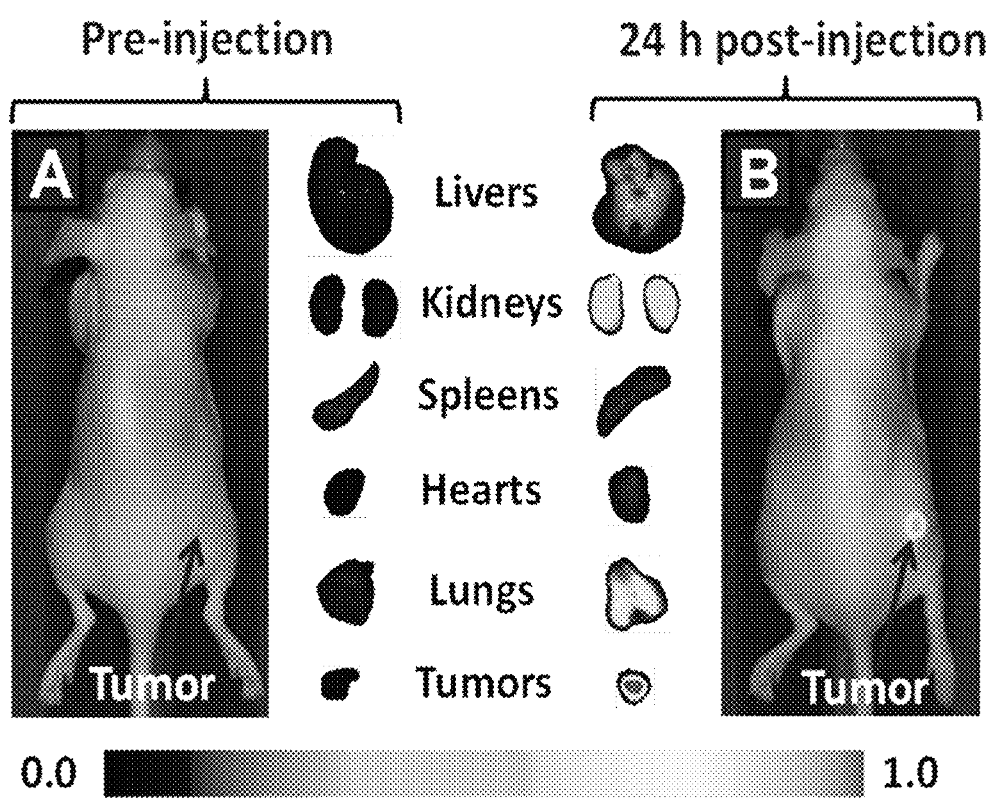
FIGS. 8A and 8B are photographs of fluorescence in vivo images of tumor-bearing mice and various organs, illustrating the organ and tumor distribution of SiNc-NP before (FIG. 8A) and 24 hours after i.v. injection (FIG. 8B) into nude mice bearing xenografts of ovarian cancer.
Figure 9:
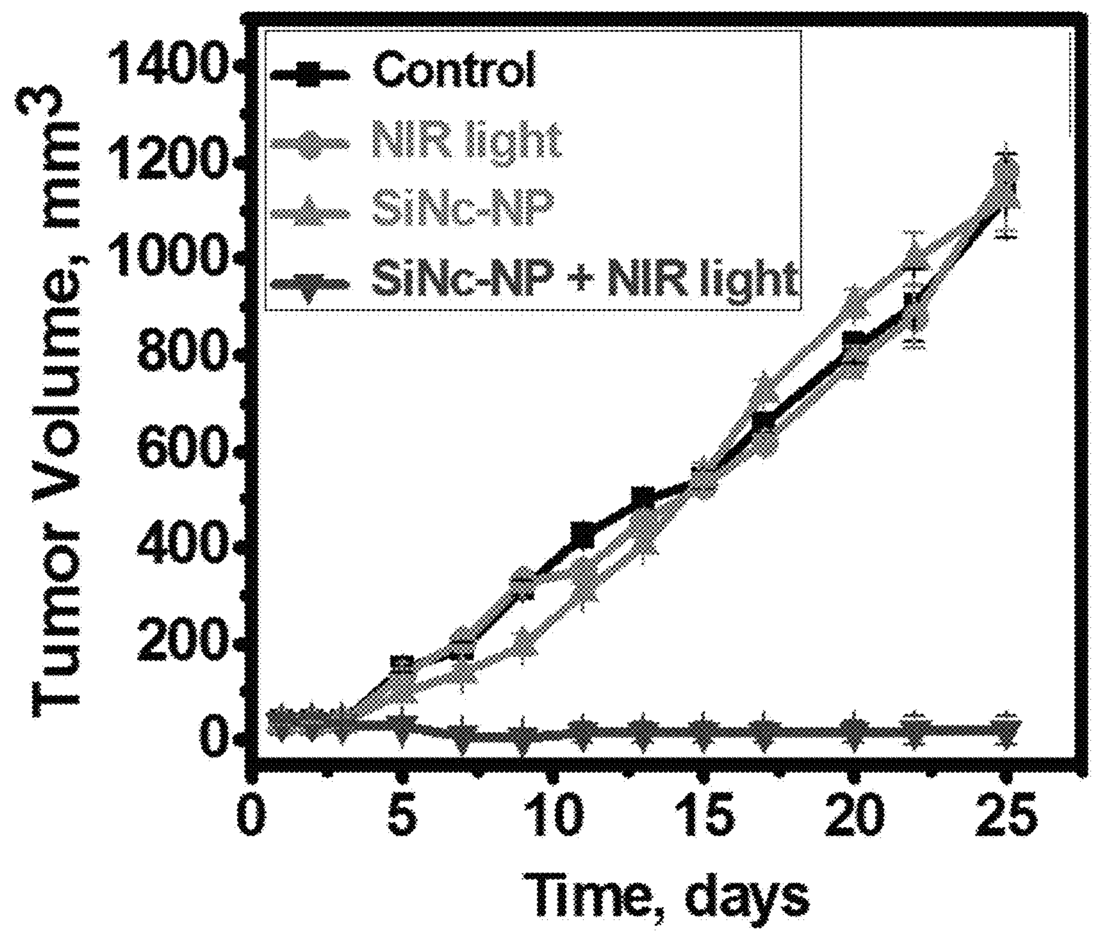
FIG. 9 is a plot of tumor volume versus time, illustrating the growth of cancer tumors in mice after treatment with a saline control, 785 nm laser diode (1.3 W/cm$^2$, 10 minutes), SiNc-NP, and combinatorial phototherapy with SiNc-NP combined with laser irradiation (1.3 W/cm$^2$, 10 minutes).
Figure 10:
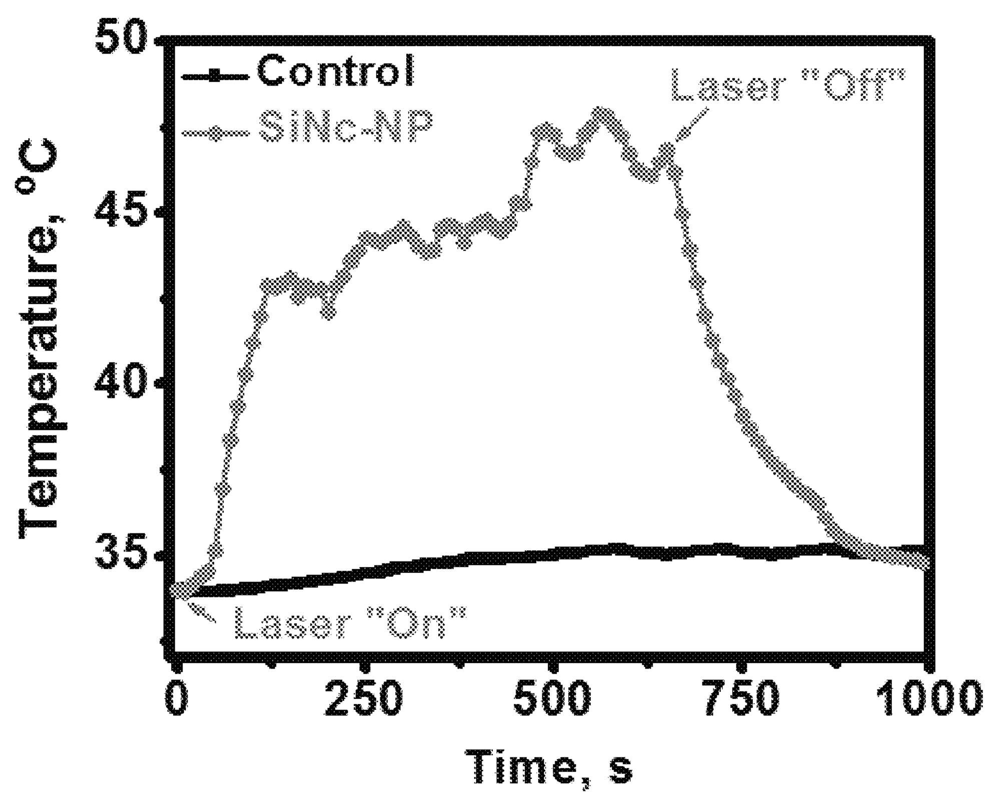
FIG. 10 is a plot of temperature versus time, illustrating the temperature changes inside the tumor treated with SiNc-NP and exposed to the 785 nm laser diode at a power density of 1.3 W/cm$^2$, with the arrows indicating when the laser diode was turned on and off, respectively.
Figure 11:
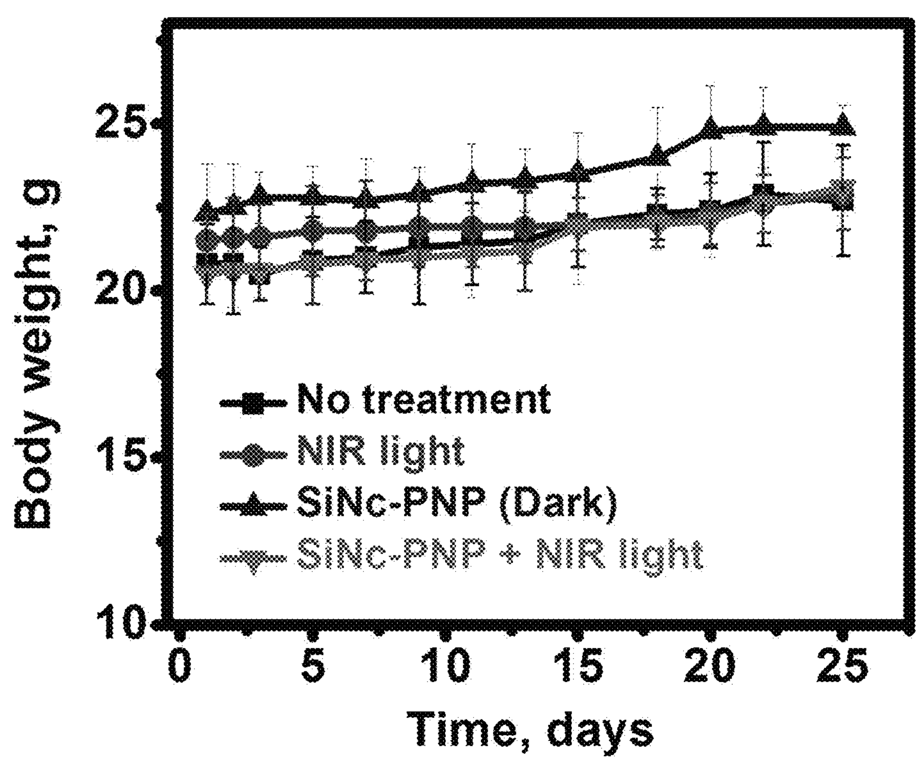
FIG. 11 is a plot of body weight versus time, illustrating the body weight curves of the mice after treatment with a saline control, 785 nm laser diode (1.3 W/cm$^2$, 10 minutes), SiNc-NP, and combinatorial phototherapy with SiNc-NP combined with laser irradiation (1.3 W/cm$^2$, 10 minutes).

The in vivo studies revealed that the developed nanoplatform can provide for SiNc delivery specifically to the cancer tumors (FIGS. 8A and 8B). Strong SiNc fluorescence was recorded mainly in the cancer tumor 24 hours after i.v. injection and only trace amounts of SiNc-NP were found in the lungs and kidneys (FIG. 8B). The strong fluorescence signal in the tumor area validated the efficiency of SiNc-NP as NIR-imaging agent for fluorescence image-guided surgery. The anticancer efficacy of the combinatorial phototherapy in nude mice bearing a doxorubicin-resistant human ovarian cancer xenograft was also confirmed. The solid tumors treated with a single dose of SiNc-NP (0.3 mg/mL) combined with 10 minutes of NIR light were completely eradicated from the mice with no evidence of cancer recurrence for 25 days post-treatment (FIG. 9). Under irradiation, the intratumoral temperature increased rapidly from 36.6° C. to about 43° C. within 1 minute, reaching about 48° C. after 10 minutes (FIG. 10, circles). In comparison, the temperature of the tumor without SiNc-NP treatment had almost no changes under the same 785 nm irradiation conditions (FIG. 10, squares). Additionally, despite the strong anticancer effect of the combinatorial phototherapy, no weigh loss was observed for treated mice, indicating that there were no side effects related to weight loss (FIG. 11).

An orthotopic ovarian cancer model was employed to further evaluated NIR fluorescence imaging properties of SiNc-NP and confirm that the higher SiNc-loaded nanoparticle SiNc-NP (0.6 mg/mL) demonstrates OFF-ON cancer imaging properties. Sufficient bioluminescence was observed throughout the peritoneal cavity in mice 2 weeks post-implantation of ES2/Luc cancer cells, indicating successful tumor engraftment as well as potential spread of metastasis (FIG. 12A).

100 μL of a 0.6 mg/mL SiNc-NP solution was delivered into mice bearing orthotopic tumors via tail vein injection. Mice treated with SiNc-NPs were housed for 24 hours and then injected with 200 μL of 10 mg/mL D-luciferin PBS solution 10 minutes before imaged in an IVIS imaging system. After full body bioluminescence and NIR fluorescence imaging, mice were euthanized and suspected tumor mass as well as major organs were harvested and imaged.

Figures 12A, 12B, 12C, 12D, 12E, 12F:
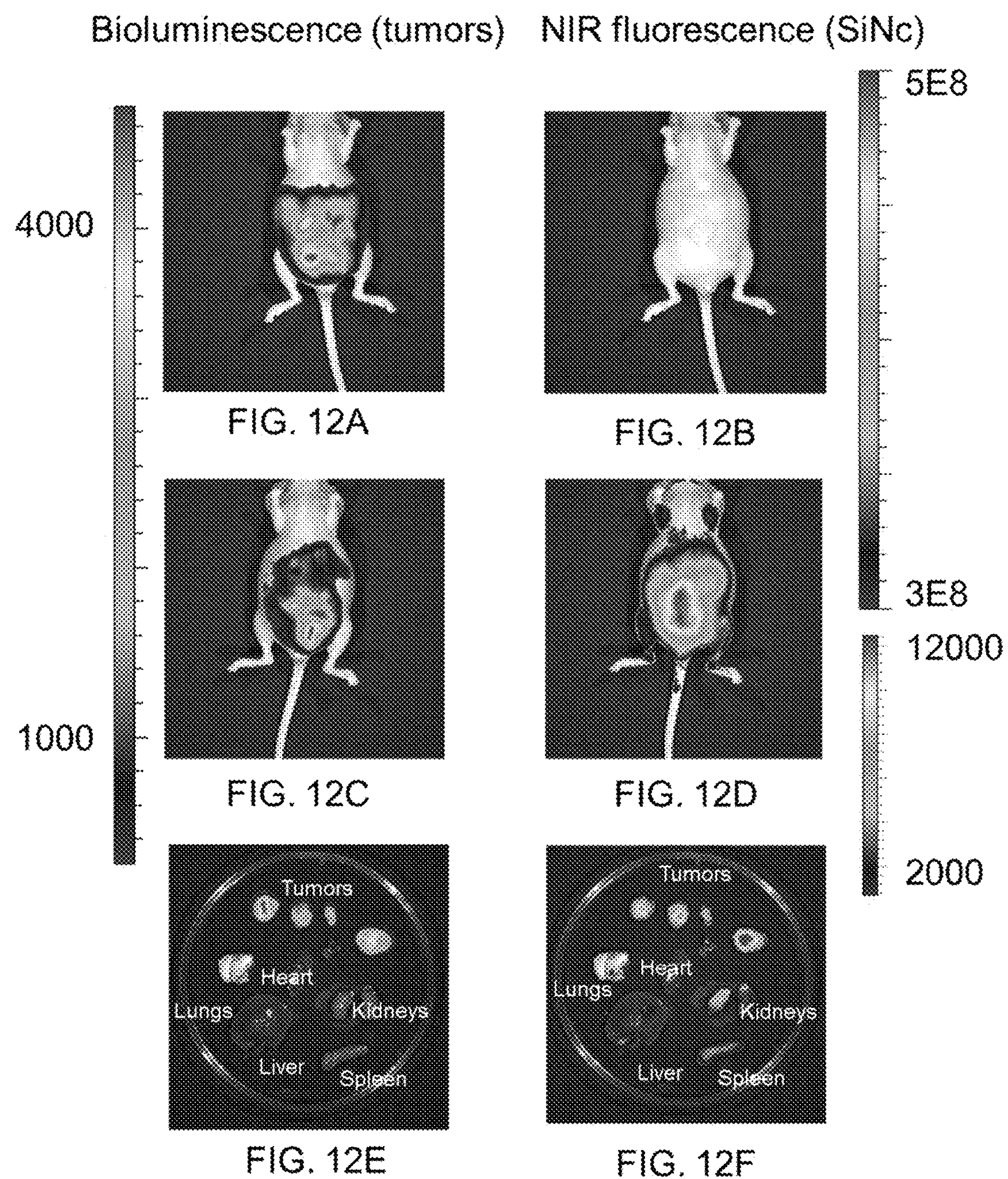
FIG. 12A is a bioluminescent image of a nude mouse immediately following administration of SiNc-NP (0.6 mg/mL) via intravenous injection, the mouse bearing ovarian orthotopic ES2/Luc tumors 2 weeks after implantation.
FIG. 12B is a fluorescent image of the mouse from FIG. 12A.
FIG. 12C is a bioluminescent image of a nude mouse 24 hours post administration of SiNc-NP (0.6 mg/mL) via intravenous injection, the mouse bearing ovarian orthotopic ES2/Luc tumors 2 weeks after implantation.
FIG. 12D is a fluorescent image of the mouse from FIG. 12C.
FIG. 12E is a bioluminescent image of tumors and organs collected from mice administered with SiNc-NP.
FIG. 12F is a fluorescent image of the tumors and organs from FIG. 12E.

Immediately after 100 μL i.v. injection of SiNc-NP (0.6 mg/mL), no visible NIR fluorescence was observed after mouse body imaging (FIG. 12B), while bioluminescence was detected in peritoneal cavity (FIG. 12A), indicating OFF fluorescence imaging state. 24 hours after i.v. injection, strong SiNc fluorescence was recorded in peritoneal cavity overlapping with bioluminescence suggesting possible accumulation of "turned-ON" SiNc at tumor sites (FIGS. 12C and 12D). After mouse was euthanized, tumors and organs were collected for further confirmation of distribution of "turned-ON" SiNc. Several clusters of white mass (tumors) were found in the peritoneal cavity, matching with the areas with strong bioluminescent intensity in FIGS. 12A and 12C. Solid masses were collected and imaged along with organs. Strong bioluminescence was recorded from all the collected masses, confirming they are indeed tumors (FIG. 12E). NIR fluorescence was captured from all tumors as well as spots on liver, spleen and kidneys (FIG. 12F) suggesting possible metastasis since bioluminescence was also present. These results confirmed that the SiNc nanoprobe was selectively targeting tumor tissue with recovered NIR fluorescence, demonstrating the capability in cancer imaging, including OFF-ON cancer fluorescence imaging, and the promising potential in image-guided surgery.

Example 10

Toxicity

Genotoxicity:

Genotoxicity describes the property of chemical agents that damages the genetic information within a cell causing mutations, which may lead to cancer. An in vitro micronucleus assay was used to determine the genotoxicity of SiNc-NP on Chinese Hamster Ovary (CHO-K1) cells. Cells were treated with SiNc-NP (90 μg/mL) for the experiment group, fresh media for negative control, or methyl methanesulfonate (MMS, 50 μg/mL) for a positive control.

Figure 13:
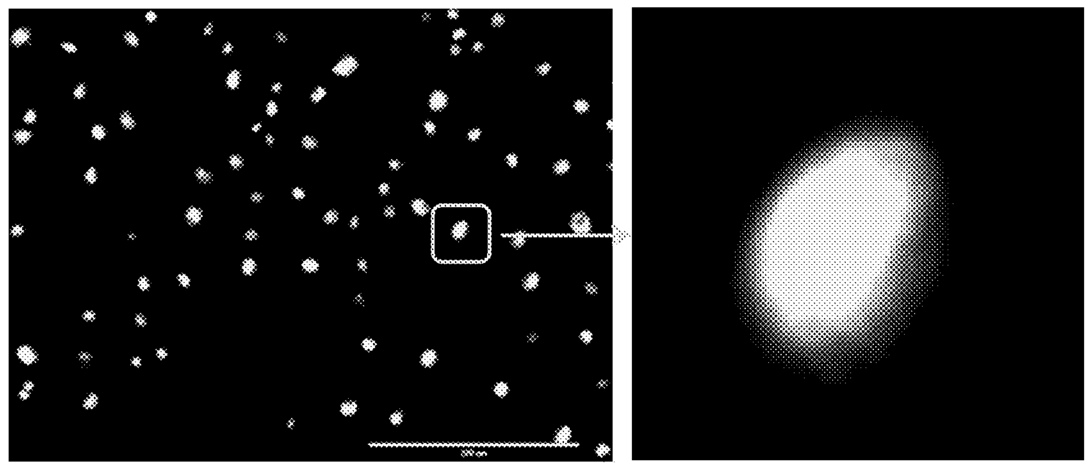
FIG. 13 is a fluorescent microscopy image of CHO-K1 cells stained with DAPI and treated with media as a negative control. The right panel shows the enlarged image from the boxed area in the left panel, and the scale bar represents 100 μm.
Figure 14:
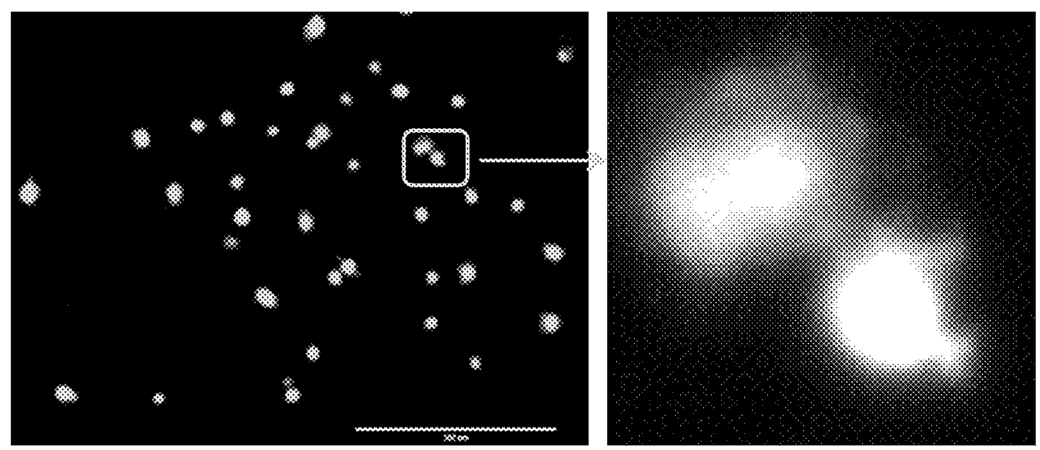
FIG. 14 is a fluorescent microscopy image of CHO-K1 cells stained with DAPI and treated with methyl methanesulfonate (MMS, 50 μg/mL) as a positive control. The right panel shows the enlarged image from the boxed area in the left panel, and the scale bar represents 100 μm.
Figure 15:
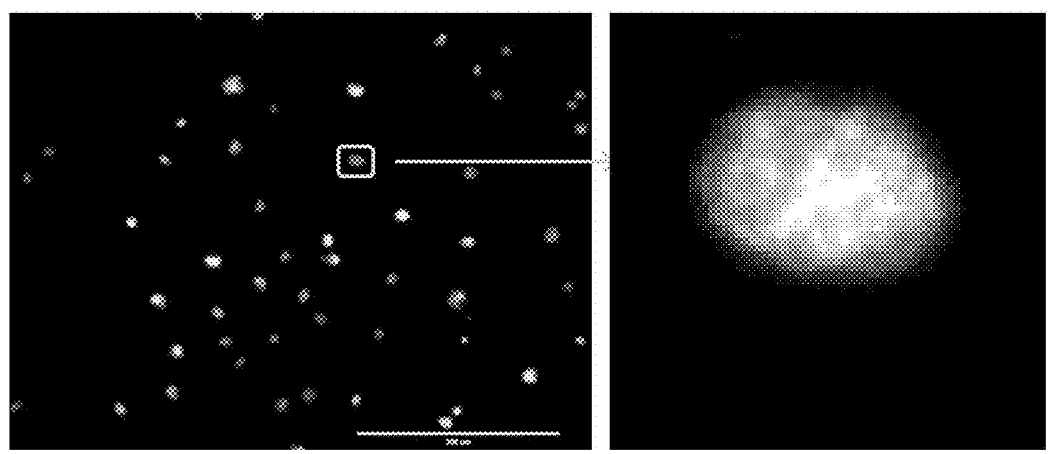
FIG. 15 is a fluorescent microscopy image of CHO-K1 cells stained with DAPI and treated with SiNc-NP (90 μg/mL) for 24 hours. The right panel shows the enlarged image from the boxed area in the left panel, and the scale bar represents 100 μm.
Figure 16:
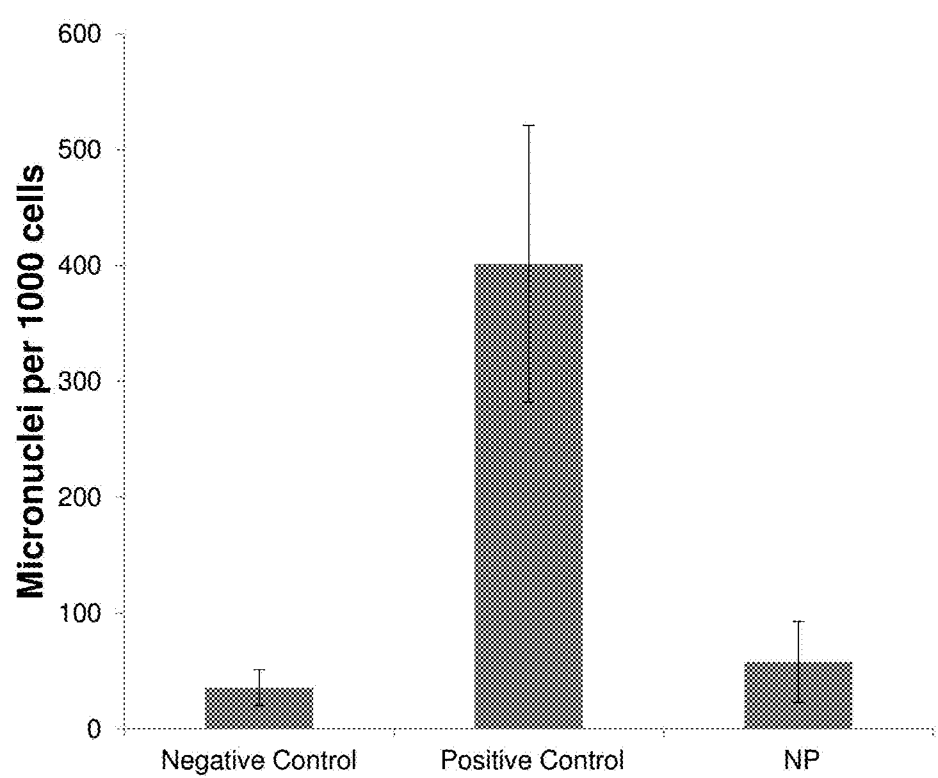
FIG. 16 is a plot of micronuclei per 1000 cells versus cell treatment, illustrating the genotoxicity of the treatments of FIGS. 13-15 as represented by the numbers of micronuclei in the cells. Error bars indicate standard deviation.
Figure 17:
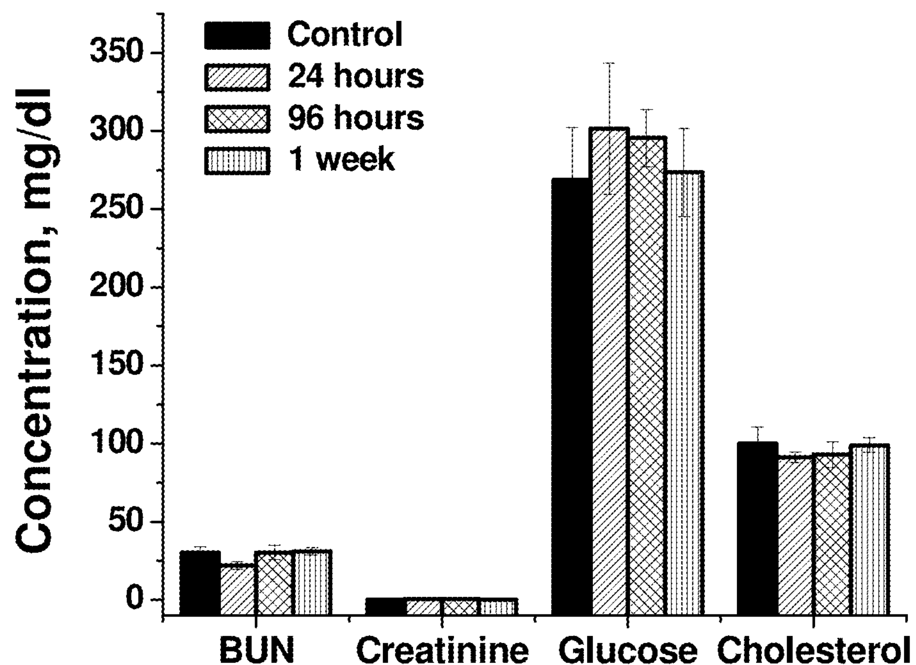
FIG. 17 is a plot of concentration versus biomarkers, illustrating the blood levels of blood urine nitrogen (BUN) and creatinine, illustrating kidney function, and glucose and cholesterol in control mice and mice administered SiNc-NP (1.5 mg/kg) by intravenous injection, assessed after 24 hours, 96 hours and 1 week.
Figure 18:
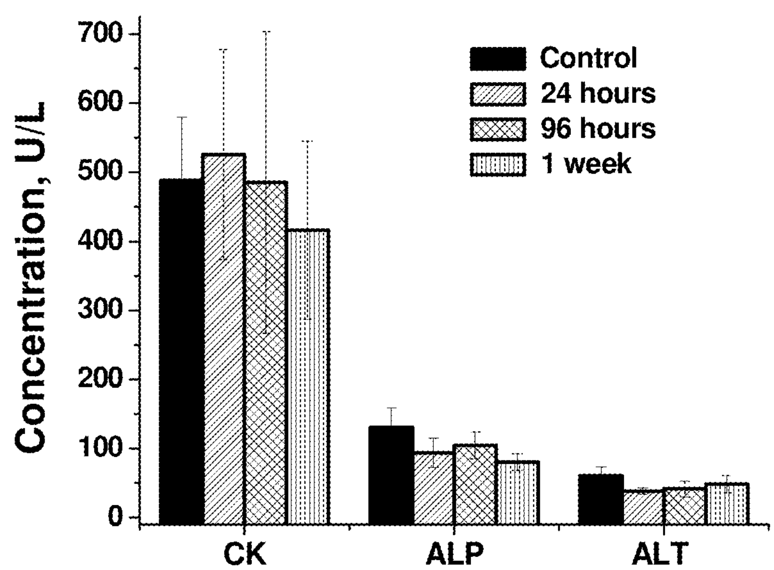
FIG. 18 is a plot of concentration versus biomarkers, illustrating the blood levels of creatine kinase (CK), illustrating cardiac function, and alanine aminotransferase (ALT) and alkaline phosphatase (ALP), illustrating liver function, of the mice from FIG. 17.
Figure 19:
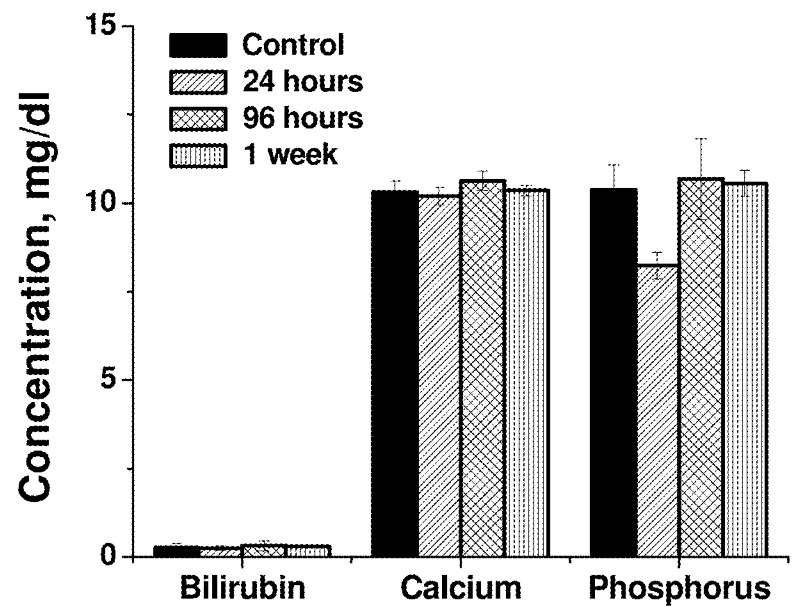
FIG. 19 is a plot of concentration versus biomarkers, illustrating the blood levels of bilirubin, calcium and phosphorus of the mice from FIG. 17.
Figure 20:
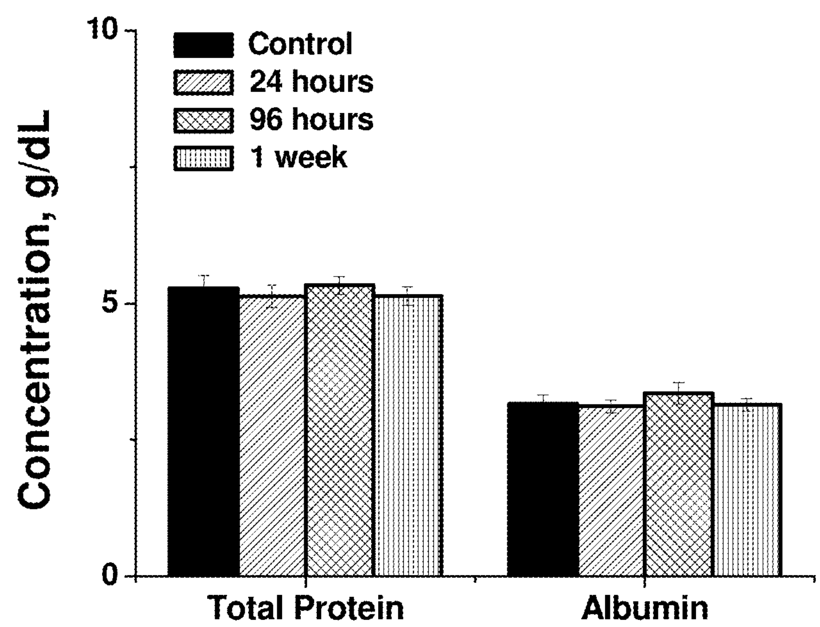
FIG. 20 is a plot of concentration versus biomarkers, illustrating the blood levels of total protein and albumin of the mice from FIG. 17.

Evaluated by florescence imaging, most cell nuclei had clear and smooth edge in the negative control group that was treated with media only, whereas in the positive group treated with MMS, noticeable numbers of small buds/fragments appeared on or near cell nuclei, representing micronuclei (FIGS. 13 and 14). These images also showed that most cell nuclei remained intact when treated with SiNc-NP (FIG. 15). A quantitative analysis was then performed to evaluate the genotoxicity. The analysis counted the number of micronuclei per 1000 cells. Each treatment group was counted in triplicate and the results are shown in FIG. 16. Compared to the negative control, SiNc-NPs did not induce increased formation of micronuclei, suggesting that the tested NP concentration was not genotoxic (FIG. 16).

Acute Toxicity:

The safety profile of SiNc-loaded PEG-PCL nanoparticles was evaluated in mice and compared to non-treated mice. None of the mice died or exhibited abnormal behavioral changes during the duration of the study. Changes in the weight during the course of the study for both the treated and untreated mice as control were monitored. Based on the data, none of the groups in either model demonstrated weight loss ≥15%, indicating that the SiNc-loaded nanoparticles did not produce acute toxicity at 1.5 mg/kg dose of SiNc and 50 mg/kg of the PEG-PCL polymer.

At time intervals of 24 hours, 96 hours and 1 week post i.v. injection (1.5 mg/kg of SiNc and 50 mg/kg of PEG-PCL polymer), mice were euthanized. Blood samples were collected, centrifuged at 3000×g for 7 minutes and the plasma samples were submitted for complete blood panel chemistry analysis at the Oregon State University Veterinary Diagnostic Laboratory. The toxicity effects of the SiNc-NP on liver, renal and heart were evaluated by measuring concentrations of surrogate markers in blood for liver function (alanine transaminase (ALT) and alkaline phosphatase (ALP)), kidney function (blood urea nitrogen (BUN) and creatinine), and heart function (creatine kinase (CK)) along with other markers (FIGS. 17-20). The measured values in non-treated mice and mice injected with the SiNc-NP were similar, indicating that there were no statistically significant differences between the treated and control groups. These results suggested that the prepared nanoplatform was safe and non-toxic. Based on the behavioral observations, weight data, and the biochemical estimations, no acute toxicity was observed with SiNc loaded PEG-PCL nanoplatform.

Figure 21:
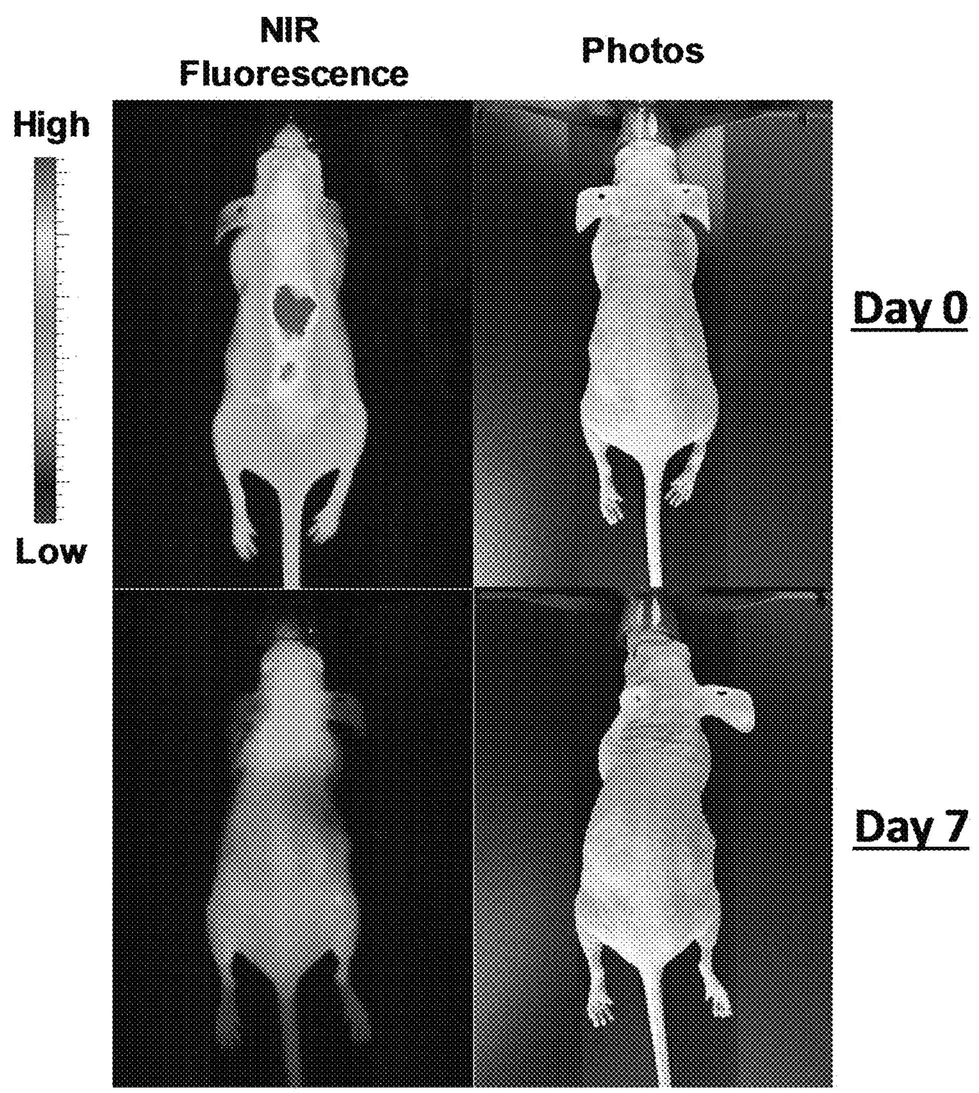
FIG. 21 is a digital image of NIR fluorescence and visible light images of nude mice on day 0 and day 7, illustrating the lack of phototoxicity of the SiNc-NP in mice after they were simultaneously injected by i.v. and subcutaneously (on the back), at a dose of 1.5 mg/kg SiNc and exposed to the simulated daylight for two hours daily during a 7 day period.

Phototoxicity:

Phototoxicity and photosensitivity of a patient's skin under daylight (sunlight) is a dominant and clinically significant side effect of phototherapy (photodynamic therapy—PDT and photothermal therapy—PTT). To determine if SiNc-NP formulation was photosafe, nude immunodeficient mice were treated by two ways simultaneously with SiNc=1.5 mg/kg; by i.v. injection and by subcutaneous injection at the back. Next, 5 treated mice vs 5 control non-treated mice were exposed to simulated sunlight for 2 hours daily for 7 days (10000 lux). Body weight and skin conditions in studied mice were monitored. No changes in behavior, weight loss or skin damage (such as redness, burns, etc.) were noticed, indicating that SiNc-NP was photosafe and does not cause phototoxicity or photosensitivity under simulated sunlight (FIG. 21).

Example 11

Synthesis of LHRH-Labelled SiNc-PNP

The LHRH-labelled activatable SiNc-PNPs were prepared using 1 (or 5, 10, 25 or 50) % w/w (LHRH-polymer/non-labeled polymer) of LHRH-PEG-PCL mixed with non-modified PEG-PCL according to the same procedure used for preparation of non-modified SiNc-PNP.

LHRH-PEG-PCL Conjugation Method:

50 mg of HOOC-PEG(5k)-PCL(10k) was dissolved in 800 μL acetonitrile. 1 mg of N,N'-Dicyclohexylcarbodiimide was dissolved in 100 μL acetonitrile and added into the polymer solution. The mixture was sonicated for 30 minutes followed by addition of 6 mg of sulfo-NHS (N-hydroxysulfosuccinimide). LHRH peptides (1:1 LHRH:PEG-PCL molar ratio) were first solubilized in 100 μL PBS (pH 8.2) and then added. The reaction mixture was sonicated for 1 hour at room temperature. 2 mL acetonitrile was added by the end of the reaction to minimize free LHRH. Clear solution was collected by centrifugation and conjugated polymer was obtained in white powders after lyophilization.

Example 12

Internalization Efficiency by Flow Cytometry

Flow cytometry was employed to evaluate internalization efficiency of the FITC-loaded LHRH-SiNc-PNP in ovarian cancer cells. After incubation for 24 hours with nanoparticles prior to flow cytometry analysis, the cells were trypsinized, collected in 0.5 mL Eppendorf tubes, washed 3 times with DPBS, resuspended in 200 μL of DPBS, and analyzed using an Accuri C6 flow cytometer (BD Biosciences, San Jose, Calif.). FITC fluorescence was collected by a 533/30 band-pass filter. All data analyses were performed using the BD C6 Accuri software.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A composition, comprising:

a polymer nanoparticle comprising a mPEG-5k-PCL-10k block copolymer; and a photosensitive compound encapsulated within the polymer nanoparticle, the photosensitive compound having a formula

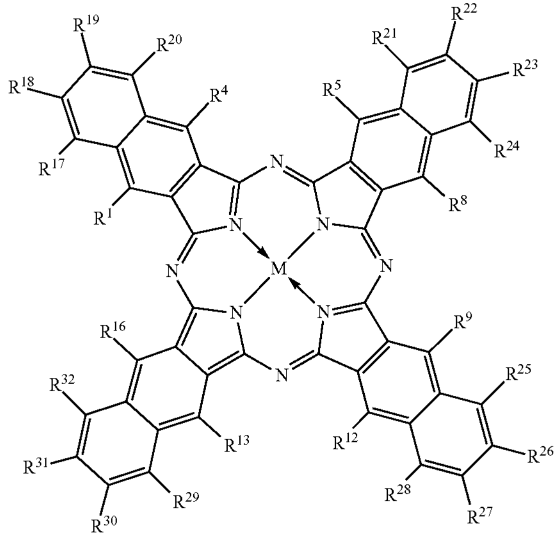

wherein $R^1$-$R^{32}$ are hydrogen; and

M is silicon substituted with two —O—Si($C_{2-10}$alkyl)$_3$.

2. The composition of claim 1, wherein the photosensitive compound is

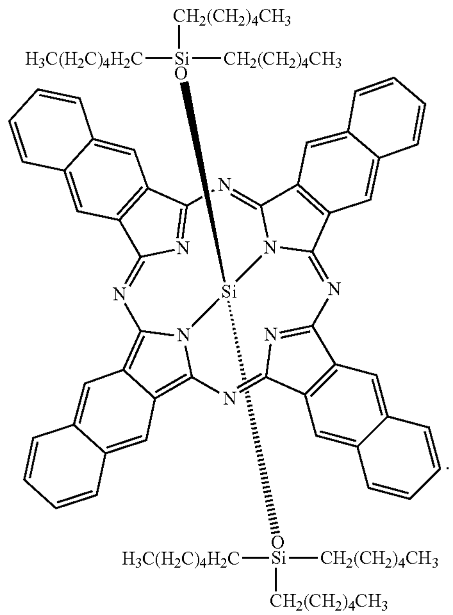

3. The composition of claim 1, wherein the photosensitive compound is loaded into the nanoparticle at a concentration of from 0.01 mg/mL to 1 mg/mL.

4. The composition of claim 3, wherein the photosensitive compound is loaded into the nanoparticle at a concentration of from 0.01 mg/mL to less than 0.4 mg/mL.

5. The composition of claim 3, wherein the photosensitive compound is loaded into the nanoparticle at a concentration of from 0.4 mg/mL to 1 mg/mL.

6. The composition of claim 1, wherein the loading efficiency of the photosensitive compound in the nanoparticle is from greater than zero to 4%.

7. The composition of claim 1, wherein the loading efficiency of the photosensitive compound in the nanoparticle is from 2% to 3.5%.

8. The composition of claim 1, wherein the loading efficiency of the photosensitive compound in the nanoparticle is from 4.5% to 8%.

9. The composition of claim 1, further comprising a luteinizing-hormone-releasing hormone (LHRH) peptide.

10. The composition of claim 9, wherein the LHRH peptide is Gln-His-Trp-Ser-Tyr-DLys(DCys)-Leu-Arg-Pro-NH-Et; Glp-His-Trp-Ser-Tyr-D-Lys-Leu-Arg-Pro-Gly-$NH_2$; or Glp-His-Trp-Ser-His-Asp-Trp-Lys-Pro-Gly-$NH_2$.

11. A pharmaceutical preparation, comprising the composition of claim 1, and a pharmaceutically acceptable excipient.

12. A method of diagnosing and/or treating a disease condition, the method comprising:

contacting a biological cell with the composition of claim 1; and exposing the cell and the composition to light.

13. The method of claim 12, further comprising detecting a fluorescent emission from the cell.

14. The method of claim 12, wherein the cell is a cancer cell.

15. The method of claim 14, wherein the cancer cell is a solid tumor cancer cell.

16. The method of claim 14, wherein the cancer cell is an ovarian cancer cell, breast cancer cell, prostate cancer cell, pancreatic cancer cell, head and neck cancer cell, liver cancer cell or skin melanoma cell.

17. The method of claim 14, wherein contacting the biological cell with the composition comprises administering the composition to a subject.

18. A composition, comprising:

a polymer nanoparticle comprising a mPEG-5k-PCL-10k block copolymer; and a photosensitive compound having a structure

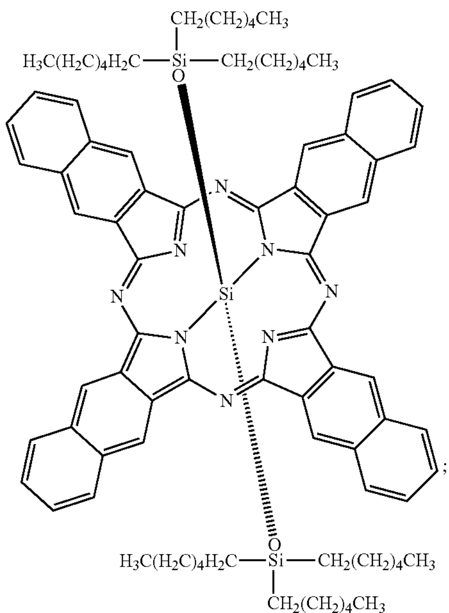

encapsulated within the polymer nanoparticle, the photosensitive compound being loaded into the nanoparticle at a concentration of from 0.4 mg/mL to 2 mg/mL.

* * * * *